(12) United States Patent  
Soni et al.

(10) Patent No.: US 9,355,534 B2  
(45) Date of Patent: May 31, 2016

(54) CAUSING DISPLAY OF A NOTIFICATION ON A WRIST WORN APPARATUS

(71) Applicant: Nokia Technologies Oy, Espoo (FI)

(72) Inventors: Shahil Soni, Espoo (FI); Apaar Tuli, Helsinki (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 14/104,654

(22) Filed: Dec. 12, 2013

(65) Prior Publication Data

US 2015/0170482 A1 Jun. 18, 2015

(51) Int. Cl.
*G08B 5/22* (2006.01)
*G06F 1/16* (2006.01)
*G06F 3/14* (2006.01)
*A61B 5/11* (2006.01)

(52) U.S. Cl.
CPC .............. *G08B 5/228* (2013.01); *G06F 1/163* (2013.01); *G06F 1/1613* (2013.01); *G06F 3/1423* (2013.01); *A61B 5/11* (2013.01); *A61B 5/1118* (2013.01); *G09G 2340/0464* (2013.01); *G09G 2370/16* (2013.01); *G09G 2380/02* (2013.01)

(58) Field of Classification Search
CPC ....... G06F 1/1613; A61B 5/1118; A61B 5/11

USPC ................. 340/539.11, 539.1, 539.12, 573.1; 361/807

See application file for complete search history.

(56) References Cited

U.S. PATENT DOCUMENTS

2012/0086573 A1* 4/2012 Bischoff et al. ............ 340/573.1
2013/0106603 A1* 5/2013 Weast et al. .............. 340/539.11
2013/0222271 A1 8/2013 Alberth et al.
2013/0271350 A1 10/2013 Lyons

OTHER PUBLICATIONS

International Search Report and Written Opinion from corresponding International Application No. PCT/FI2014/050968 dated Aug. 21, 2015.

* cited by examiner

*Primary Examiner* — Steven Lim
*Assistant Examiner* — Hongmin Fan
(74) *Attorney, Agent, or Firm* — Alston & Bird LLP

(57) ABSTRACT

A method comprising determining of a notification based, at least in part, on occurrence of an event, the notification comprising a notification type associated with the event, causing display of a representation of the notification at a position on a wrist adherence portion of a wrist worn apparatus, the wrist adherence portion being distinct from a primary display, and the representation of the notification being indicative of the notification type, receiving information indicative of a notification selection input associated with the notification, and causing display of a different representation of the notification on the primary display of the wrist worn apparatus based, at least in part, on the notification selection input is disclosed.

19 Claims, 9 Drawing Sheets

CAUSING DISPLAY OF A NOTIFICATION ON A WRIST WORN APPARATUS

TECHNICAL FIELD

The present application relates generally to causing display of a representation of a notification on a wrist worn apparatus.

BACKGROUND

As electronic apparatuses play an increasing role in the lives of their users, it has become increasingly desirable to allow for interaction between the user and the electronic apparatus in a manner that allows the user to quickly and easily understand information conveyed by the electronic apparatus. For example, it may be desirable to allow a user to determine what information is being communicated to the user at a glance, while the user is engaged in other activities, when circumstances are not optimal for concentrated viewing, and/or the like.

SUMMARY

Various aspects of examples of the invention are set out in the claims.

One or more embodiments may provide an apparatus, a computer readable medium, a non-transitory computer readable medium, a computer program product, and a method for determining of a notification based, at least in part, on occurrence of an event, the notification comprising a notification type associated with the event, causing display of a representation of the notification at a position on a wrist adherence portion of a wrist worn apparatus, the wrist adherence portion being distinct from a primary display, and the representation of the notification being indicative of the notification type, receiving information indicative of a notification selection input associated with the notification, and causing display of a different representation of the notification on the primary display of the wrist worn apparatus based, at least in part, on the notification selection input.

One or more embodiments may provide an apparatus, a computer readable medium, a computer program product, and a non-transitory computer readable medium having means for determining of a notification based, at least in part, on occurrence of an event, the notification comprising a notification type associated with the event, means for causing display of a representation of the notification at a position on a wrist adherence portion of a wrist worn apparatus, the wrist adherence portion being distinct from a primary display, and the representation of the notification being indicative of the notification type, means for receiving information indicative of a notification selection input associated with the notification, and means for causing display of a different representation of the notification on the primary display of the wrist worn apparatus based, at least in part, on the notification selection input.

In at least one example embodiment, the display of the representation of the notification at the position on the wrist adherence portion of the wrist worn apparatus comprises display of the representation of the notification at the position on a wrist adherence portion display of the wrist adherence portion of the wrist worn apparatus.

In at least one example embodiment, the different representation of the notification comprises text information associated with the notification.

One or more example embodiments further perform identification of the notification attribute associated with the notification.

In at least one example embodiment, a color of the representation of the notification is indicative of at least one notification attribute associated with the notification.

In at least one example embodiment, the color of the representation of the notification is indicative of at least one of a level of urgency, a time, an application, an importance, a count of associated notifications, a notification status, or the notification type.

In at least one example embodiment, the notification type is indicative of at least one of an application event, a system event, a text event, a call event, an emergency event, or a transportation event.

In at least one example embodiment, the notification comprises a notification status, and further comprising determination of the position of the representation of the notification on the wrist adherence portion of the wrist worn apparatus based, at least in part, on the notification status.

One or more example embodiments further perform determination that the notification status of the notification has changed to a different notification status, determination of a different position of the representation of the notification on the wrist adherence portion of the wrist worn apparatus based, at least in part, on the different notification status, and causation of display of the representation of the notification at the different position on the wrist adherence portion of the wrist worn apparatus.

One or more example embodiments further perform termination of display of the representation of the notification at the position on the wrist adherence portion of the wrist worn apparatus.

In at least one example embodiment, the notification status indicates that the notification has not been displayed, and the different notification status indicates that the notification has been displayed.

In at least one example embodiment, the determination that the notification status of the notification has changed to the different notification status is based, at least in part, on the causation of display of the different representation of the notification on the primary display.

In at least one example embodiment, the determination that the notification status of the notification has changed to the different notification status is based, at least in part, on the receipt of information indicative of the notification selection input associated with the notification.

One or more example embodiments further perform receipt of information indicative of the notification being read, and wherein the determination that the notification status of the notification has changed to a different notification status is based, at least in part, on the information indicative of the notification being read.

One or more example embodiments further perform receipt of information indicative of the change of the notification status of the notification to the different notification status from a separate apparatus, and wherein the determination that the notification status of the notification has changed to a different notification status is based, at least in part, on the information indicative of the change of the notification status of the notification to the different notification status.

In at least one example embodiment, the position of the representation of the notification on the wrist adherence portion of the wrist worn apparatus is proximate to a side of the primary display, and the different position of the representation of the notification on the wrist adherence portion of the wrist worn apparatus is proximate to an opposite side of the primary display.

In at least one example embodiment, the position that is proximate to the side of the primary display is a position that is closer to an edge of the wrist adherence portion of the wrist worn apparatus that is proximate to the primary display than another edge of the wrist adherence portion, and the position that is proximate to the opposite side of the primary display is a position that is closer to an edge of the wrist adherence portion of the wrist worn apparatus that is proximate to the primary display than another edge of the wrist adherence portion.

In at least one example embodiment, the position of the representation of the notification on the wrist adherence portion of the wrist worn apparatus is a position on a first band portion, and the different position of the representation of the notification on the wrist adherence portion of the wrist worn apparatus is a position on a second band portion.

In at least one example embodiment, the notification status indicates a level of urgency of the notification, and the determination of the position of the representation of the notification on the wrist adherence portion of the wrist worn apparatus is further based, at least in part, on the level of urgency.

In at least one example embodiment, the position of the representation of the notification on the wrist adherence portion of the wrist worn apparatus is proximate to a side of the primary display in circumstances where the notification status indicates a level of urgency that satisfies a threshold level of urgency, and the position of the representation of the notification on the wrist adherence portion of the wrist worn apparatus is proximate to an opposite side of the primary display in circumstances where the notification status indicates a different level of urgency of the notification that fails to satisfy the threshold level of urgency.

In at least one example embodiment, the position of the representation of the notification on the wrist adherence portion of the wrist worn apparatus is a position on a first band portion in circumstances where the notification status indicates a level of urgency that satisfies a threshold level of urgency, and the position of the representation of the notification on the wrist adherence portion of the wrist worn apparatus is a position on a second band portion in circumstances where the notification status indicates a different level of urgency of the notification that fails to satisfy the threshold level of urgency.

In at least one example embodiment, wherein the notification selection input is a tap input at a position on the wrist adherence portion of the wrist worn apparatus that corresponds with the position of the representation of the notification on the wrist adherence portion of the wrist worn apparatus.

In at least one example embodiment, the wrist adherence portion is a housing that is configured to at least partially surround a wrist of a wearer, and the primary display is coupled with the wrist adherence portion.

In at least one example embodiment, the primary display is coupled with a primary display housing and the wrist adherence portion is coupled with the primary display housing.

In at least one example embodiment, the wrist adherence portion comprises a band.

In at least one example embodiment, the band comprises a first band portion and a second band portion, such that the first band portion and the second band portion are detachable from each other.

In at least one example embodiment, the band comprises at least two band segments.

In at least one example embodiment, the band segment is a band link.

In at least one example embodiment, the position on the wrist adherence portion is a spatial position on the wrist adherence portion.

In at least one example embodiment, the position on the wrist adherence portion is identified by a row and a column.

In at least one example embodiment, a row is spatial grouping corresponding with an axis of the wrist adherence portion, and a column is a spatial grouping corresponding with another axis of the wrist adherence portion.

In at least one example embodiment, the display of the representation of the notification at the position identified by the row and the column on the wrist adherence portion is based, at least in part, on at least one notification attribute associated with the notification.

In at least one example embodiment, the position on the wrist adherence portion is indicative of the notification attribute.

In at least one example embodiment, at least one of the row or the column is indicative of the notification attribute.

In at least one example embodiment, the notification attribute identifies at least one of a notification time, a notification status, or the notification type.

In at least one example embodiment, the display of the representation of the notification at the position on the wrist adherence portion corresponding with the row is based, at least in part, on a notification time.

In at least one example embodiment, the position on the wrist adherence portion corresponding with the row is indicative of chronological adjacency between the notification and an adjacent position in the row.

In at least one example embodiment, the display of the representation of the notification at the position on the wrist adherence portion corresponding with the column is based, at least in part, on a notification time.

In at least one example embodiment, the position on the wrist adherence portion corresponding with the column is indicative of chronological adjacency between the notification and an adjacent position in the column.

In at least one example embodiment, the display of the representation of the notification at the position on the wrist adherence portion corresponding with the row is based, at least in part, on a notification status.

In at least one example embodiment, the display of the representation of the notification at the position on the wrist adherence portion corresponding with the column is based, at least in part, on a notification status.

In at least one example embodiment, the display of the representation of the notification at the position on the wrist adherence portion corresponding with the row is based, at least in part, on the notification type.

In at least one example embodiment, the display of the representation of the notification at the position on the wrist adherence portion corresponding with the row is indicative of the notification type.

In at least one example embodiment, the display of the representation of the notification at the position on the wrist adherence portion corresponding with the column is based, at least in part, on the notification type.

In at least one example embodiment, the display of the representation of the notification at the position on the wrist adherence portion corresponding with the column is indicative of the notification type.

BRIEF DESCRIPTION OF THE DRAWINGS

For a more complete understanding of embodiments of the invention, reference is now made to the following descriptions taken in connection with the accompanying drawings in which.

DETAILED DESCRIPTION OF THE DRAWINGS

Figure 1:
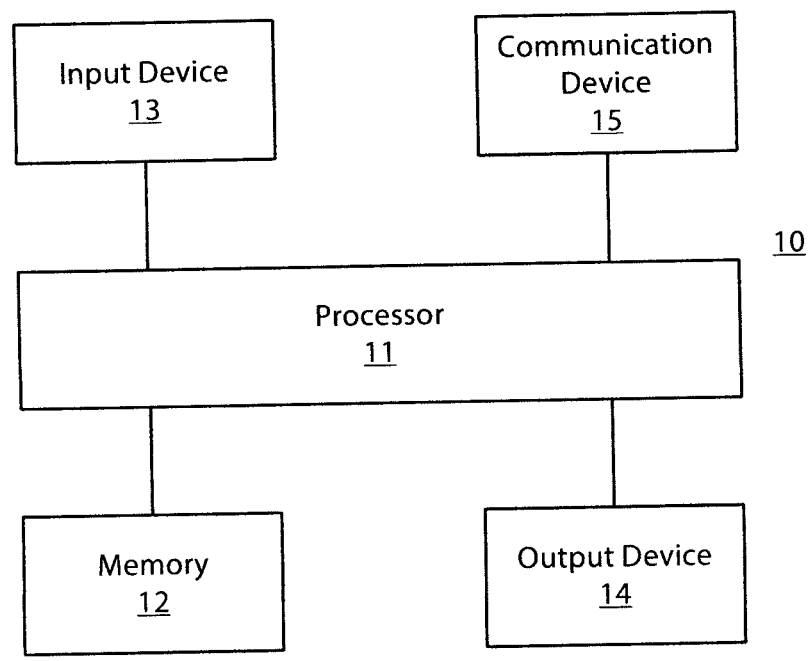
FIG. 1 is a block diagram showing an apparatus according to at least one example embodiment.

An embodiment of the invention and its potential advantages are understood by referring to FIGS. 1 through 8 of the drawings.

Some embodiments will now be described more fully hereinafter with reference to the accompanying drawings, in which some, but not all, embodiments are shown. Various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information," and similar terms may be used interchangeably to refer to data capable of being transmitted, received and/or stored in accordance with embodiments of the present invention. Thus, use of any such terms should not be taken to limit the spirit and scope of embodiments of the present invention.

Additionally, as used herein, the term 'circuitry' refers to (a) hardware-only circuit implementations (e.g., implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a microprocessor(s) or a portion of a microprocessor(s), that require software or firmware for operation even if the software or firmware is not physically present. This definition of 'circuitry' applies to all uses of this term herein, including in any claims. As a further example, as used herein, the term 'circuitry' also includes an implementation comprising one or more processors and/or portion(s) thereof and accompanying software and/or firmware. As another example, the term 'circuitry' as used herein also includes, for example, a baseband integrated circuit or applications processor integrated circuit for a mobile phone or a similar integrated circuit in a server, a cellular network apparatus, other network apparatus, and/or other computing apparatus.

As defined herein, a "non-transitory computer-readable medium," which refers to a physical medium (e.g., volatile or non-volatile memory device), can be differentiated from a "transitory computer-readable medium," which refers to an electromagnetic signal.

FIG. 1 is a block diagram showing an apparatus, such as an electronic apparatus 10, according to at least one example embodiment. It should be understood, however, that an electronic apparatus as illustrated and hereinafter described is merely illustrative of an electronic apparatus that could benefit from embodiments of the invention and, therefore, should not be taken to limit the scope of the invention. While electronic apparatus 10 is illustrated and will be hereinafter described for purposes of example, other types of electronic apparatuses may readily employ embodiments of the invention. Electronic apparatus 10 may be a personal digital assistant (PDAs), a pager, a mobile computer, a desktop computer, a television, a gaming apparatus, a laptop computer, a tablet computer, a media player, a camera, a video recorder, a mobile phone, a wearable apparatus, a wrist worn apparatus, a watch apparatus, a global positioning system (GPS) apparatus, an automobile, a kiosk, an electronic table, and/or any other types of electronic systems. Moreover, the apparatus of at least one example embodiment need not be the entire electronic apparatus, but may be a component or group of components of the electronic apparatus in other example embodiments. For example, the apparatus may be an integrated circuit, a set of integrated circuits, and/or the like.

Furthermore, apparatuses may readily employ embodiments of the invention regardless of their intent to provide mobility. In this regard, even though embodiments of the invention may be described in conjunction with mobile applications, it should be understood that embodiments of the invention may be utilized in conjunction with a variety of other applications, both in the mobile communications industries and outside of the mobile communications industries. For example, the apparatus may be, at least part of, a non-carryable apparatus, such as a large screen television, an electronic table, a kiosk, an automobile, and/or the like.

In at least one example embodiment, electronic apparatus 10 comprises processor 11 and memory 12. Processor 11 may be any type of processor, controller, embedded controller, processor core, and/or the like. In at least one example embodiment, processor 11 utilizes computer program code to cause an apparatus to perform one or more actions. Memory 12 may comprise volatile memory, such as volatile Random Access Memory (RAM) including a cache area for the temporary storage of data and/or other memory, for example, non-volatile memory, which may be embedded and/or may be removable. The non-volatile memory may comprise an EEPROM, flash memory and/or the like. Memory 12 may store any of a number of pieces of information, and data. The information and data may be used by the electronic apparatus 10 to implement one or more functions of the electronic apparatus 10, such as the functions described herein. In at least one example embodiment, memory 12 includes computer program code such that the memory and the computer program code are configured to, working with the processor, cause the apparatus to perform one or more actions described herein.

The electronic apparatus 10 may further comprise a communication device 15. In at least one example embodiment, communication device 15 comprises an antenna, (or multiple antennae), a wired connector, and/or the like in operable communication with a transmitter and/or a receiver. In at least one example embodiment, processor 11 provides signals to a transmitter and/or receives signals from a receiver. The signals may comprise signaling information in accordance with a communications interface standard, user speech, received data, user generated data, and/or the like. Communication device 15 may operate with one or more air interface standards, communication protocols, modulation types, and access types. By way of illustration, the electronic communication device 15 may operate in accordance with second-generation (2G) wireless communication protocols IS-136 (time division multiple access (TDMA)), Global System for Mobile communications (GSM), and IS-95 (code division multiple access (CDMA)), with third-generation (3G) wireless communication protocols, such as Universal Mobile Telecommunications System (UMTS), CDMA2000, wideband CDMA (WCDMA) and time division-synchronous CDMA (TD-SCDMA), and/or with fourth-generation (4G) wireless communication protocols, wireless networking protocols, such as 802.11, short-range wireless protocols, such as Bluetooth, and/or the like. Communication device 15 may operate in accordance with wireline protocols, such as Ethernet, digital subscriber line (DSL), asynchronous transfer mode (ATM), and/or the like.

Processor 11 may comprise means, such as circuitry, for implementing audio, video, communication, navigation, logic functions, and/or the like, as well as for implementing embodiments of the invention including, for example, one or more of the functions described herein. For example, processor 11 may comprise means, such as a digital signal processor device, a microprocessor device, various analog to digital converters, digital to analog converters, processing circuitry and other support circuits, for performing various functions including, for example, one or more of the functions described herein. The apparatus may perform control and signal processing functions of the electronic apparatus 10 among these devices according to their respective capabilities. The processor 11 thus may comprise the functionality to encode and interleave message and data prior to modulation and transmission. The processor 1 may additionally comprise an internal voice coder, and may comprise an internal data modem. Further, the processor 11 may comprise functionality to operate one or more software programs, which may be stored in memory and which may, among other things, cause the processor 11 to implement at least one embodiment including, for example, one or more of the functions described herein. For example, the processor 11 may operate a connectivity program, such as a conventional internet browser. The connectivity program may allow the electronic apparatus 10 to transmit and receive internet content, such as location-based content and/or other web page content, according to a Transmission Control Protocol (TCP), Internet Protocol (IP), User Datagram Protocol (UDP), Internet Message Access Protocol (IMAP), Post Office Protocol (POP), Simple Mail Transfer Protocol (SMTP), Wireless Application Protocol (WAP), Hypertext Transfer Protocol (HTTP), and/or the like, for example.

The electronic apparatus 10 may comprise a user interface for providing output and/or receiving input. The electronic apparatus 10 may comprise an output device 14. Output device 14 may comprise an audio output device, such as a ringer, an earphone, a speaker, and/or the like. Output device 14 may comprise a tactile output device, such as a vibration transducer, an electronically deformable surface, an electronically deformable structure, and/or the like. Output device 14 may comprise a visual output device, such as a display, a light, and/or the like. In at least one example embodiment, the apparatus causes display of information, the causation of display may comprise displaying the information on a display comprised by the apparatus, sending the information to a separate apparatus that comprises a display, and/or the like. The electronic apparatus may comprise an input device 13. Input device 13 may comprise a light sensor, a proximity sensor, a microphone, a touch sensor, a force sensor, a button, a keypad, a motion sensor, a magnetic field sensor, a camera, and/or the like. A touch sensor and a display may be characterized as a touch display. In an embodiment comprising a touch display, the touch display may be configured to receive input from a single point of contact, multiple points of contact, and/or the like. In such an embodiment, the touch display and/or the processor may determine input based, at least in part, on position, motion, speed, contact area, and/or the like. In at least one example embodiment, the apparatus receives an indication of an input. The apparatus may receive the indication from a sensor, a driver, a separate apparatus, and/or the like. The information indicative of the input may comprise information that conveys information indicative of the input, indicative of an aspect of the input indicative of occurrence of the input, and/or the like.

The electronic apparatus 10 may include any of a variety of touch displays including those that are configured to enable touch recognition by any of resistive, capacitive, infrared, strain gauge, surface wave, optical imaging, dispersive signal technology, acoustic pulse recognition or other techniques, and to then provide signals indicative of the location and other parameters associated with the touch. Additionally, the touch display may be configured to receive an indication of an input in the form of a touch event which may be defined as an actual physical contact between a selection object (e.g., a finger, stylus, pen, pencil, or other pointing device) and the touch display. Alternatively, a touch event may be defined as bringing the selection object in proximity to the touch display, hovering over a displayed object or approaching an object within a predefined distance, even though physical contact is not made with the touch display. As such, a touch input may comprise any input that is detected by a touch display including touch events that involve actual physical contact and touch events that do not involve physical contact but that are otherwise detected by the touch display, such as a result of the proximity of the selection object to the touch display. A touch display may be capable of receiving information associated with force applied to the touch screen in relation to the touch input. For example, the touch screen may differentiate between a heavy press touch input and a light press touch input. In at least one example embodiment, a display may display two-dimensional information, three-dimensional information and/or the like.

In embodiments including a keypad, the keypad may comprise numeric (for example, 0-9) keys, symbol keys (for example, #, *), alphabetic keys, and/or the like for operating the electronic apparatus 10. For example, the keypad may comprise a conventional QWERTY keypad arrangement. The keypad may also comprise various soft keys with associated functions. In addition, or alternatively, the electronic apparatus 10 may comprise an interface device such as a joystick or other user input interface.

Input device 13 may comprise a media capturing element. The media capturing element may be any means for capturing an image, video, and/or audio for storage, display or transmission. For example, in at least one example embodiment in which the media capturing element is a camera module, the camera module may comprise a digital camera which may form a digital image file from a captured image. As such, the camera module may comprise hardware, such as a lens or other optical component(s), and/or software necessary for creating a digital image file from a captured image. Alternatively, the camera module may comprise only the hardware for viewing an image, while a memory device of the electronic apparatus 10 stores instructions for execution by the processor 11 in the form of software for creating a digital image file from a captured image. In at least one example embodiment, the camera module may further comprise a processing element such as a co-processor that assists the processor 11 in processing image data and an encoder and/or decoder for compressing and/or decompressing image data. The encoder and/or decoder may encode and/or decode according to a standard format, for example, a Joint Photographic Experts Group (JPEG) standard format.

FIGS. 2A-2D are diagrams illustrating wrist worn apparatuses according to at least one example embodiment. The examples of FIGS. 2A-2D are merely examples and do not limit the scope of the claims. For example, wrist worn apparatus design may vary, wrist adherence portion configuration may vary, mechanical coupling may vary, wrist worn apparatus configuration may vary, primary display configuration may vary, and/or the like.

As electronic apparatuses become more prevalent, many users may desire to interact with electronic apparatuses in manners that are intuitive, convenient, accessible, and/or the like. For example, a user may desire to interact with an electronic apparatus that may be unobtrusive to interact with, convenient to interact with, and/or the like. In at least one example embodiment, an apparatus is a wrist worn apparatus. A wrist worn apparatus may be a watch apparatus, a bracelet apparatus, and/or the like. In at least one example embodiment, a wrist worn apparatus comprises a wrist adherence portion. In at least one example embodiment, the wrist adherence portion is a part of the housing of the wrist worn apparatus that is configured to cause the wrist worn apparatus to adhere to a user's wrist, avoid falling from the user's wrist, and/or the like. For example, the wrist adherence portion may be a housing that is configured to at least partially surround a wrist of a wearer of the wrist worn apparatus. In such an example, the wrist adherence portion may be a band, a strap, a bracelet, and/or the like. The wrist adherence portion of the wrist worn apparatus may be rigid, flexible, stretchy, foldable, curvable, deformable, bendable, and/or the like. For example, the wrist adherence portion of the wrist worn apparatus may be a non-curved band that a user can configure such that the non-curved band curves and wraps around the wrist of the user.

In many circumstances, a user may desire to have a wrist worn apparatus display information. For example, the user may desire the wrist worn apparatus to display information of particular interest to the user, to display visual information that may appeal to the user, and/or the like. In at least one example embodiment, a wrist adherence portion of a wrist worn apparatus comprises a wrist adherence portion display. For example, the wrist adherence portion display may be a light emitting diode display, an electronic ink display, a liquid crystal display, an organic light emitting diode display, and/or the like. In such an example, the wrist adherence portion display may be flexible, rigid, deformable, foldable, and/or the like.

Figure 2A:
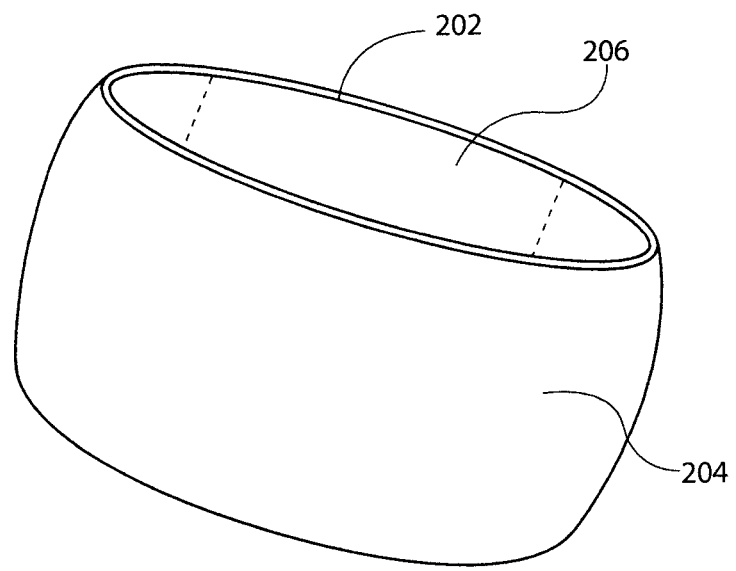
FIGS. 2A-2D are diagrams illustrating wrist worn apparatuses according to at least one example embodiment.

FIG. 2A is a diagram illustrating a wrist worn apparatus. In the example of FIG. 2A, wrist worn apparatus 202 is a bracelet apparatus. In the example of FIG. 2A, the wrist adherence portion of wrist worn apparatus 202 is the entirety of wrist worn apparatus 202. In the example of FIG. 2A, wrist worn apparatus 202 comprises a single continuous housing. Although the example of FIG. 2A illustrates wrist worn apparatus 202 as a single continuous housing, wrist worn apparatus 202 may be a single discontinuous housing such that a gap exists between two separate ends of wrist worn apparatus 202. Wrist worn apparatus 212 may be rigid, flexible, stretchy, deformable, and/or the like. In the example of FIG. 2A, wrist adherence portion 204 and wrist adherence portion 206 are comprised by wrist worn apparatus 202. For example, as depicted in FIG. 2A, wrist adherence portion 204 may be the portion of wrist worn apparatus 202 shown between the dashed lines, and wrist adherence portion 206 may be the smaller portion of wrist worn apparatus 202 shown between the dashed lines. Wrist adherence portion 204 may comprise a wrist adherence portion display. For example, the wrist adherence portion display may extend to the edges of wrist worn apparatus 202, may be bound by margins between an edges of wrist adherence portion 204 and the edges of wrist worn apparatus 202, and/or the like. The wrist adherence portion display may extend across the entirety of wrist adherence portion 204, extend across a portion of wrist adherence portion 204, and/or the like. Wrist adherence portion 204 may comprise a single flexible display, a plurality of flexible displays, a plurality of rigid displays, and/or the like. For example, a part of wrist adherence portion 204 may comprise a flexible light emitting diode display and a different part of wrist adherence portion 204 may comprise a rigid liquid crystal display.

In some circumstances, a user may desire to have a wrist worn apparatus display information that may not be tailored for display on a wrist adherence portion display, suited for display on a particular type of wrist adherence portion display, and/or the like. For example, the user may desire to view high resolution, full color visual information that may not be tailored for display on a light emitting diode wrist adherence portion display that may have a limited display resolution, limited range of color reproduction, and/or the like. In another example, the user may desire to view an animated image that may not be suitable for display on a black and white electronic ink display that may have a limited display resolution, restricted refresh rate, and/or the like. In some circumstances, a user may desire to have information displayed by way of a wrist worn apparatus in such a way that may permit display of a full color representation of information, may allow the user to perceive visual information at a level of detail beyond what a wrist adherence portion display may be configured to provide, and/or the like. In at least one example embodiment, an apparatus comprises a primary display. The primary display may be a light emitting diode display, an electronic ink display, a liquid crystal display, an organic light emitting diode display, and/or the like. In at least one example embodiment, a primary display is a central display of a wrist worn apparatus. In at least one example embodiment, a primary display is a display characterized by a rendering quality that is greater than a rendering quality of a wrist adherence portion display. For example, the primary display by be characterized by a greater display resolution, a larger display size, a broader color reproduction range, and/or the like.

Figure 2B:
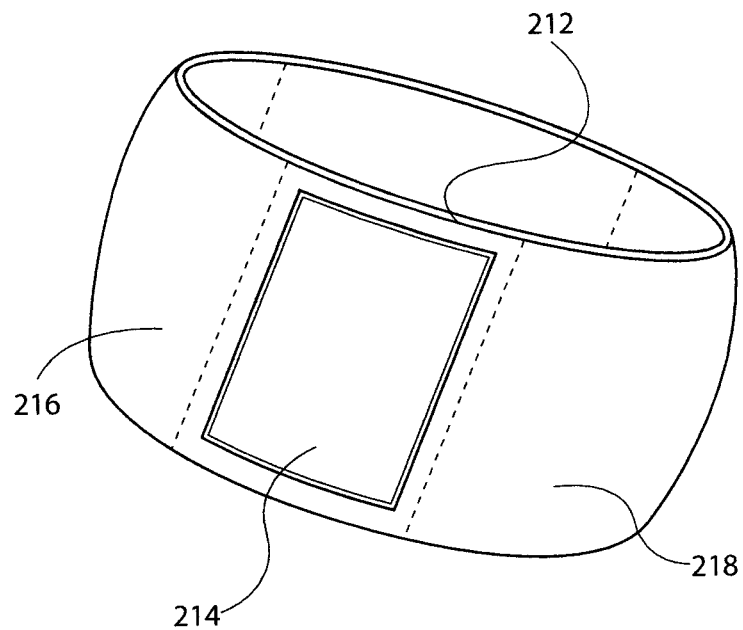

FIG. 2B is a diagram illustrating a wrist worn apparatus according to at least one example embodiment. In at least one example embodiment, a primary display is coupled with a wrist adherence portion of a wrist worn apparatus. For example, the primary display may be housed within the wrist worn apparatus, housed within the wrist adherence portion of the wrist worn apparatus, and/or the like. In the example of FIG. 2B, wrist worn apparatus 212 comprises a single continuous housing. Although the example of FIG. 2B illustrates wrist worn apparatus 212 as a single continuous housing, wrist worn apparatus 212 may be a single discontinuous housing such that a gap exists between two separate ends of wrist worn apparatus 212. Wrist worn apparatus 212 may be rigid, flexible, stretchy, deformable, and/or the like. In the example of FIG. 2B, wrist worn apparatus 212 comprises wrist adherence portions 216 and 218. As illustrated in the example of FIG. 2B, wrist adherence portions 216 and 218 are two distinct portions of wrist worn apparatus 212 and are separated by primary display 214. Each of wrist adherence portions 216 and 218 may comprise a single flexible display, a plurality of flexible displays, a plurality of rigid displays, and/or the like. For example, a wrist adherence portion 216 may comprise a flexible light emitting diode display and wrist adherence portion 218 may comprise another flexible light emitting diode display. Primary display 214 may be a light emitting diode display, an electronic ink display, a liquid crystal display, an organic light emitting diode display, and/or the like.

In some circumstances, a user may desire to swap out a wrist adherence portion of a wrist worn apparatus for a different wrist adherence portion. For example, the user may desire to switch from a rigid plastic band to a flexible rubber band, to switch from a band comprising a flexible liquid crystal display to a different band comprising a flexible light emitting diode display, and/or the like. In such an example, the user may desire to transfer a primary display from the band to the different band. In at least one example embodiment, a primary display is coupled with a primary display housing. In such an example embodiment, the wrist adherence portion of the wrist worn apparatus may be coupled with the primary display housing such that a user may separate the primary display housing from the wrist adherence portion and couple the primary display housing to a different wrist adherence portion.

Figure 2C:
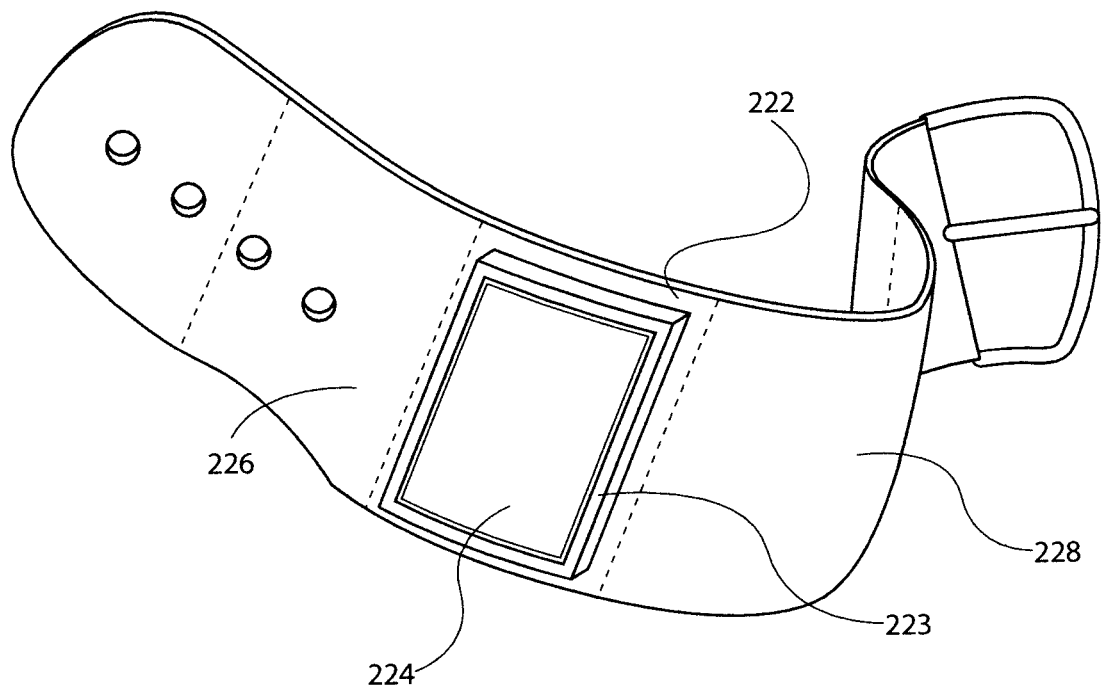

FIG. 2C is a diagram illustrating a wrist worn apparatus according to at least one example embodiment. In the example of FIG. 2C, wrist worn apparatus 222 comprises primary display housing 223, wrist adherence portion 226, and wrist adherence portion 228. As depicted in the example of FIG. 2C, wrist worn apparatus 222 comprises a wrist adherence portion that comprises a buckle-type adherence mechanism for securing around the wrist of a user. Although the example of FIG. 2C illustrates wrist worn apparatus 222 as a single discontinuous housing, wrist worn apparatus 222 may be a single continuous housing as depicted in FIG. 2A and FIG. 2B. Wrist worn apparatus 222 may be rigid, flexible, stretchy, deformable, and/or the like. In the example of FIG. 2C, wrist worn apparatus 222 comprises wrist adherence portions 226 and 228. As illustrated in the example of FIG. 2C, wrist adherence portions 226 and 228 are two parts of wrist worn apparatus 222 and are separated by primary display housing 223. Each of wrist adherence portions 226 and 228 may comprise a single flexible display, a plurality of flexible displays, a plurality of rigid displays, and/or the like. For example, a wrist adherence portion 226 may comprise a flexible organic light emitting diode display and wrist adherence portion 228 may comprise a liquid crystal display. In the example of FIG. 2C, primary display 223 is couple with primary display housing 224. For example, primary display 224 may be removable from wrist worn apparatus 222 by way of decoupling of primary display housing 223 from wrist worn apparatus 222. Primary display 224 may be a light emitting diode display, an electronic ink display, a liquid crystal display, an organic light emitting diode display, and/or the like.

Figure 2D:
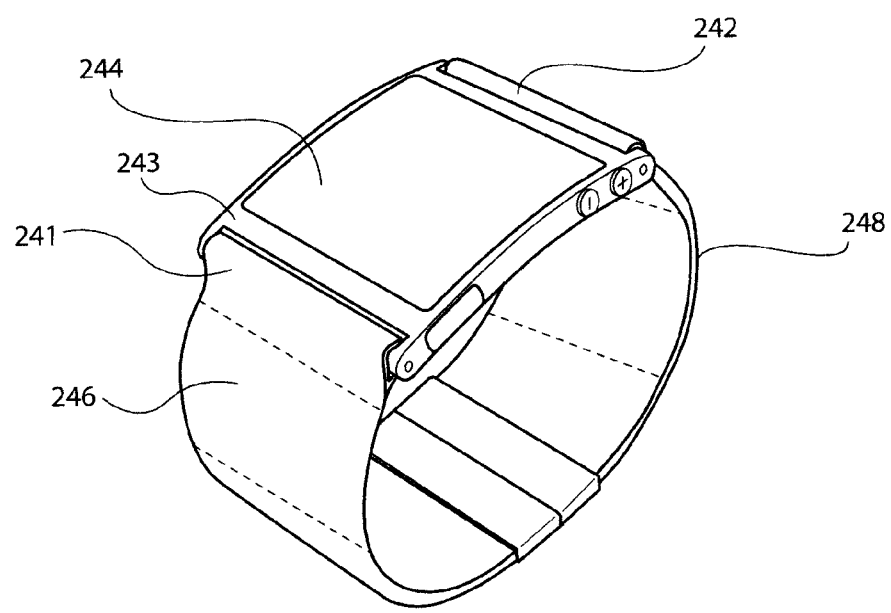

FIG. 2D is a diagram illustrating a wrist worn apparatus according to at least one example embodiment. In at least one example embodiment, a band comprises two or more band segments. For example, a band segment may be a band link, a band half, and/or the like. In such an example, the band segment may be rigid, flexible, stretchy, and/or the like. Each band segment may comprise one or more wrist adherence portion displays. In at least one example embodiment, a band comprises a first band portion and a second band portion. In such an example embodiment, the first band portion and the second band portion may be configured such that the band portions are detachable from each other.

The example of FIG. 2D depicts a wrist worn apparatus that comprises band portion 241, band portion 242, and primary display housing 243. In the example of FIG. 2D, primary display housing 243 is coupled with primary display 244. Primary display 244 may be a light emitting diode display, an electronic ink display, a liquid crystal display, an organic light emitting diode display, and/or the like. As illustrated in the example of FIG. 2D, band portion 241 and band portion 242 are separable from primary display housing 243. For example, the axis pin that is rotatably coupling band portion 241 to primary display housing 243 may be removed such that band portion 241 may be separated from primary housing 243. Although the example of FIG. 2D depicts band portion 241 as rotatably coupled with primary display housing 243, band portion 241 may be rigidly coupled with primary display housing 243, flexibly coupled with primary display housing 243, and/or the like. In the example of FIG. 2D, band portion 241 is connected to band portion 242. For example, band portion 241 and 242 may be connected around the wrist of a user of the wrist worn apparatus. As depicted in the example of FIG. 2D, band portions 241 and 242 are connected by way of a mechanical band coupling, such as a clasp, a buckle, and/or the like. Band portion 214 and 242 are configured such that the band portions are detachable at the mechanical band coupling. In the example of FIG. 2D, band portion 241 comprises wrist adherence portion 246. Wrist adherence portion 246 may comprise one or more wrist adherence portion displays. For example, wrist adherence portion 246 may comprise a flexible light emitting diode display, two rigid liquid crystal displays, and/or the like. In the example of FIG. 2D, band portion 242 comprises wrist adherence portion 248. Wrist adherence portion 248 may comprise one or more wrist adherence portion displays. For example, wrist adherence portion 248 may comprise a flexible light emitting diode display, two rigid liquid crystal displays, and/or the like.

Figure 3A:
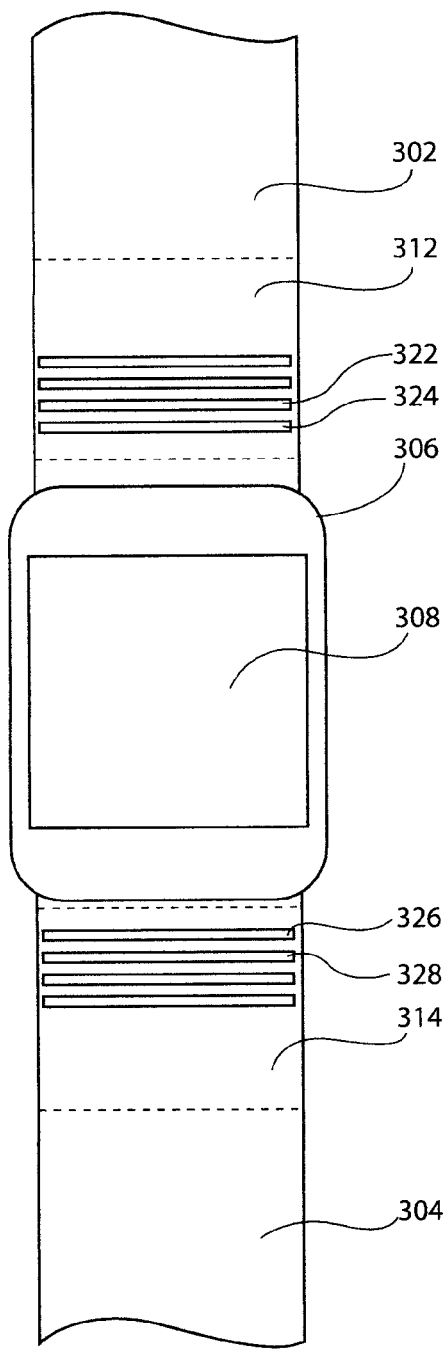
FIGS. 3A-3B are diagrams illustrating wrist worn apparatuses and representations of notifications according to at least one example embodiment.
Figure 3B:
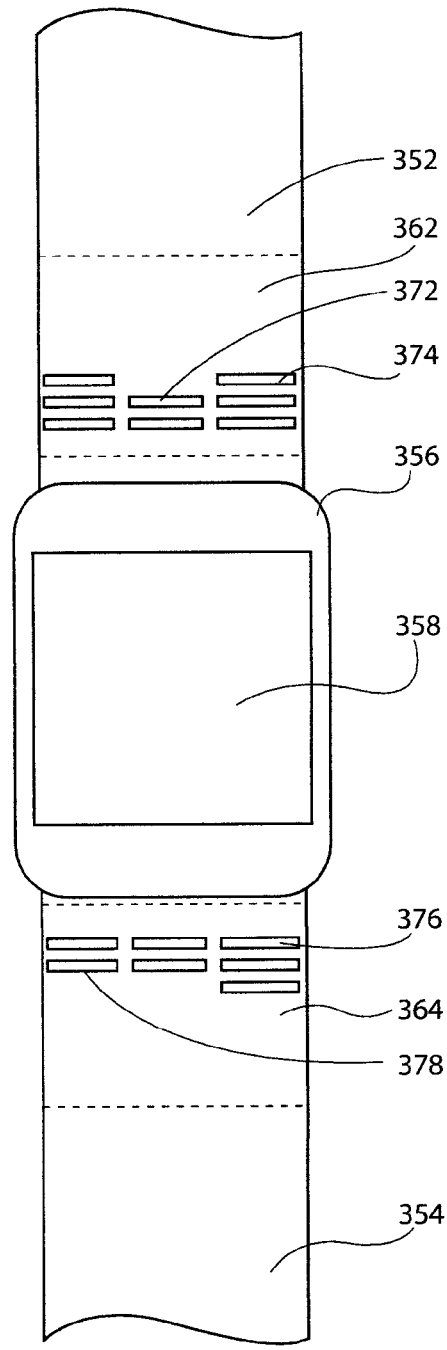

FIGS. 3A-3B are diagrams illustrating wrist worn apparatuses and representations of notifications according to at least one example embodiment. The examples of FIGS. 3A-3B are merely examples and do not limit the scope of the claims. For example, wrist worn apparatus design may vary, wrist adherence portion configuration may vary, mechanical coupling may vary, wrist worn apparatus configuration may vary, primary display configuration may vary, notifications may vary, representation of notifications may vary, notification configuration may vary, display of notifications may vary, and/or the like.

FIG. 3A is a diagram illustrating a wrist worn apparatus and representations of notifications according to at least one example embodiment. The example of FIG. 3A depicts a wrist worn apparatus comprising wrist adherence portion 302, wrist adherence portion 304, and primary display housing 306. Primary display housing 306 comprises primary display 308. In the example of FIG. 3A, wrist adherence portion 304 is a first band portion and wrist adherence portion 302 is a second band portion. In the example of FIG. 3A, wrist adherence portion 304 comprises wrist adherence display 314, and wrist adherence portion 302 comprises wrist adherence portion display 312. Each of representations 322, 324, 326, and 328 is a representation of a notification. As depicted in the example of FIG. 3A, representations 326 and 328 are displayed at a position on wrist adherence portion 304, and representations 322 and 324 are displayed at a position on wrist adherence portion 302.

FIG. 3B is a diagram illustrating a wrist worn apparatus and representations of notifications according to at least one example embodiment. The example of FIG. 3B depicts a wrist worn apparatus comprising wrist adherence portion 352, wrist adherence portion 354, and primary display housing 356. Primary display housing 356 comprises primary display 358. In the example of FIG. 3B, wrist adherence portion 354 is a first band portion and wrist adherence portion 352 is a second band portion. In the example of FIG. 3B, wrist adherence portion 354 comprises wrist adherence display 364, and wrist adherence portion 352 comprises wrist adherence portion display 362. Each of representations 372, 374, 376, and 378 is a representation of a notification. As depicted in the example of FIG. 3B, representations 376 and 378 are displayed at a position on wrist adherence portion 354, and representations 372 and 374 are displayed at a position on wrist adherence portion 352.

From time to time, miscellaneous events may occur. In such circumstances, a user of an electronic apparatus may find it desirable to be alerted of the occurrence of an event via one or more of the user's electronic apparatuses. In at least one example embodiment, an event is an application event, a system event, a text event, a call event, an emergency event, a transportation event, and/or the like. For example, receipt of an incoming phone call on an apparatus may be a call event. Receipt of a text message may be a text event. Receipt of a social networking message by way of a social networking application may be an application event. Reaching twenty-percent battery capacity may be a system event.

In certain circumstances, it may be desirable to associate an event with a notification. For example, a user may be alerted as to an occurrence of an event by way of an associated notification. In at least one example embodiment, an apparatus determines a notification based, at least in part, on occurrence of an event. In such an example embodiment, the notification may comprise a notification type associated with the event. The notification type may indicate a type of event that the notification is associated with. For example, the notification type may an application event, a system event, a text event, a call event, an emergency event, or a transportation event, and/or the like. A notification may, for example, comprise a notification dialog, a message dialog, a data feed entry, an auditory alert, a visual alert, and/or the like.

In some circumstances, a user may find it desirable to be alerted of the occurrence of an event associated with an apparatus, a separate apparatus, and/or the like, via an associated notification. For example, the user may find it desirable to view the notification by way of the user's apparatus. For example, information indicative of the notification may be displayed on the user's apparatus, rendered by the user's apparatus, and/or the like. In many circumstances, a user of a wrist worn apparatus may be unable to quickly and accurately identify a notification that is displayed on the wrist worn apparatus. For example, a primary display of the wrist worn apparatus may display a notification. Due to restrictions associated with display size, display resolution, movement of the display, etc., a user may not be able to identify the notification. For example, the viewing angle between the user and the wrist worn apparatus may be undesirable, the viewing distance between the user and the wrist worn apparatus may be too great, the amount of motion may cause the user to perceive a blurred display, and/or the like. In many circumstances, a user of a wrist worn apparatus may desire to be able to perceive a notification associated with the wrist worn apparatus such that the user is able to quickly and accurately determine the nature of the notification, basic information associated with the notification, and/or the like.

For example, a user of a wrist worn apparatus may desire to have a representation of a notification displayed by way of a display on a band of the wrist worn apparatus. The representation of the notification may be configured such that the user may identify information associated with the notification by merely glancing at the representation of the notification. In at least one example embodiment, an apparatus causes display of a representation of a notification on a wrist adherence portion of a wrist worn apparatus. For example, the apparatus may display the representation of the notification on the wrist adherence portion of the wrist worn apparatus, may send information indicative of the representation of the notification to a separate apparatus for display, and/or the like. In such an example embodiment, the wrist adherence portion may be distinct from a primary display of the wrist worn apparatus. In at least one example embodiment, the representation of the notification is indicative of a notification type associated with the event. In at least one example embodiment, an apparatus displays a representation of a notification on a wrist adherence portion display of a wrist adherence portion of a wrist worn apparatus.

In many circumstances, a user may desire to be aware of the status of a notification. For example, the user may desire to be able to distinguish a newer notification from an older notification, a notification that has been viewed from a notification that has yet to be viewed, a notification that has been displayed from a notification that has not been displayed, and/or the like. In at least one example embodiment, a notification comprises a notification status. A notification status may indicate a read status of the notification, an acknowledgement status of the notification, a display status of the notification, a priority status of the notification, and/or the like. In at least one example embodiment, a notification may comprise a notification status that indicates that a notification has not been displayed, or a different notification status that indicates that the notification has been displayed. In one or more example embodiments, a notification status indicates a level of urgency of a notification. For example, a notification may comprise a notification status that may indicate a high level of urgency, a low level of urgency, a neutral level of urgency, and/or the like. In such an example, a notification associated with an impending deadline may be associated with a higher level of urgency than a different notification associated with a social media comment. In this manner, the notification status of a notification permits the user to distinguish pertinent information associated with the notification such that the user may better decide whether to read the notification immediately, acknowledge the notification later, act on the information associated with the notification, and/or the like.

In order to facilitate identification of a notification by way of a representation of the notification, it may be desirable to convey information associated with the notification by way of the representation of the notification. In at least one example embodiment, an apparatus identifies a notification attribute associated with a notification. In such an example embodiment, the notification attribute may identify a level of urgency, a time, an application, an importance, a count of associated notifications, a notification status, a notification type, and/or the like. For example, a representation of a notification may be based, at least in part, on a notification attribute associated with the notification. In this manner, a user that perceives the representation of the notification can determine information associated with the notification by way of the representation of the notification conveying the notification attribute to the user. For example, a color of a representation of a notification may indicate at least one notification attribute associated with the notification. For example, the color of the representation may indicate a level of urgency, a time, an application, an importance, a count of associated notifications, a notification status, a notification type, and/or the like. For example, a blue representation of a notification may indicate a notification type associated with a text event. In another example, a red representation of a notification may indicate a high level of importance.

Figure 4A:
FIGS. 4A-4B are diagrams illustrating information for display on a primary display of a wrist worn apparatus according to at least one example embodiment.
Figure 4B:
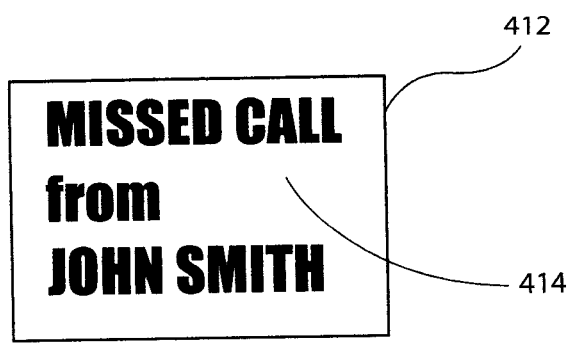

It some circumstances, it may be desirable to convey additional information by way of displaying a representation of a notification at a particular position on a wrist adherence portion of a wrist worn apparatus. For example, a representation of a notification displayed above and adjacent to a representation of a different notification may indicate that the notification is more important than the different notification, that the notification is more recent that the different notification, that the notification is less urgent that the different notification, and/or the like. In at least one example embodiment, an apparatus causes display of a representation of a notification at a position on a wrist adherence portion of a wrist worn apparatus. In at least one example embodiment, a position on a wrist adherence portion of a wrist worn apparatus is a spatial position on the wrist adherence portion of the wrist worn apparatus. In one or more example embodiments, a position on the wrist adherence portion is identified by a row and a column. In such an example embodiment, the row may be spatial grouping corresponding with an axis of the wrist adherence portion, and the column may be a spatial grouping corresponding with another axis of the wrist adherence portion. For example, a row on the wrist adherence portion of the wrist worn apparatus may be a spatial grouping extending from a side of the wrist adherence portion to an opposite side of the wrist adherence portion. In such an example, a column on the wrist adherence portion of the wrist worn apparatus may be a spatial grouping extending lengthwise along the wrist adherence portion. For example, as depicted in FIG. 4A, four representations of notifications are displayed in a four row, one column arrangement on wrist adherence portion 302. The example of FIG. 4B depicts eight representations of notifications that are displayed in a three row, three column arrangement. As can be seen in FIGS. 4A-4B, the rows extend horizontally across the band portion, and the columns extend laterally along the band portion. In at least one example embodiment, an apparatus causes display of a representation of a notification at a position identified by a row and a column on a wrist adherence portion based, at least in part, on at least one notification attribute associated with the notification. For example, the position on the wrist adherence portion may be indicative of the notification attribute, the row on the wrist adherence portion may be indicative of the notification attribute, the column on the wrist adherence portion may be indicative of the notification attribute, and/or the like.

In some circumstances, it may be desirable to organize the display of representations of notifications such that a user viewing the representations of the notifications may derive substantive information regarding the notifications, context surrounding the notifications, and/or the like. For example, a user may desire to determine, at a glance, a chronological aspect associated with the notifications, a chronological relationship between two or more notifications, and/or the like. In such an example, a row of representations of notifications on a wrist adherence portion of a wrist worn apparatus may represent a chronological time sequence of events associated with the notifications. In at least one example embodiment, an apparatus determines a position of a representation of a notification on a wrist adherence portion of a wrist worn apparatus based, at least in part, on a notification time. In at least one example embodiment, an apparatus causes display of a representation of a notification at a position on a wrist adherence portion corresponding with a row based, at least in part, on a notification time associated with the notification. A notification time may, for example, be a time associated with occurrence of an event associated with the notification, a time associated with determination of the notification, and/or the like. For example, a representation of a notification displayed at a position corresponding with a row may indicate a notification time, and a representation of a different notification displayed at a position corresponding with a different row may indicate a different notification time. The position on the wrist adherence portion corresponding with the row may indicate a chronological adjacency between the notification and an adjacent position in the different row. For example, a representation of a notification may be caused to be displayed within the same column and in a row that is adjacent to a representation of a different notification. In such an example, adjacency of the representation of the notification and the representation of the different notification may indicate that the notification is associated with an event that occurred chronologically prior to a different event associated with the different notification, chronologically after the different event, and/or the like. For example, as depicted in FIG. 4A, representations 322 and 324 are displayed within the same column and in adjacent rows on wrist adherence portion 302. Representation 322 may represent a notification pertaining to an event, and representation 324 may represent a different notification pertaining to a different event. The adjacency between representation 322 and 324 may indicate that the event occurred chronologically before the different event, chronologically after the different event, and/or the like.

In some circumstances, it may be desirable to organize the display of representations of notifications such that a user viewing the representations of the notifications may derive substantive information regarding the notifications, context surrounding the notifications, and/or the like. For example, a user may desire to determine, at a glance, a chronological aspect associated with the notifications, a chronological relationship between two or more notifications, and/or the like. In such an example, a column of representations of notifications on a wrist adherence portion of a wrist worn apparatus may represent a chronological time sequence of events associated with the notifications. In at least one example embodiment, an apparatus causes display of a representation of a notification at a position on a wrist adherence portion corresponding with a column based, at least in part, on a notification time associated with the notification. A notification time may, for example, be a time associated with occurrence of an event associated with the notification, a time associated with determination of the notification, and/or the like. For example, a representation of a notification displayed at a position corresponding with a column may indicate a notification time, and a representation of a different notification displayed at a position corresponding with a different column may indicate a different notification time. The position on the wrist adherence portion corresponding with the column may indicate a chronological adjacency between the notification and an adjacent position in the column. For example, a representation of a notification may be caused to be displayed within the same column and adjacent to a representation of a different notification on the wrist adherence portion of the wrist worn apparatus. In such an example, the adjacency of the representation of the notification and the representation of the different notification may indicate that the notification is associated with an event that occurred chronologically prior to a different event associated with the different notification, chronologically after the different event, and/or the like. In this manner, the column may represent a chronological time sequence of events displayed at positions corresponding with the column.

In some circumstances, it may be desirable to display a representation of a notification at a position such that the position is indicative of a status of the notification. For example, a user may desire to be able to identify status-related information relating to a notification at a glance such that the user is better able to assess the importance of the notification, the urgency of the notification, and/or the like. In at least one example embodiment, an apparatus determines a position of a representation of a notification on a wrist adherence portion of a wrist worn apparatus based, at least in part, on a notification status. For example, an apparatus may determine a position of a representation of a notification on a wrist adherence portion of a wrist worn apparatus based, at least in part, on a level of urgency. For example, a notification associated with a storm warning may indicate a high level of urgency and, thus, may be displayed at a position that is more prominent than a different position associated with a lower level of urgency.

In some circumstances, it may be desirable to arrange display of representations of notifications within a row based, at least in part, on notification status. For example, some users may be able to quickly distinguish between several notifications displayed in a row based, at least in part, on notification status. In at least one example embodiment, an apparatus causes display of a representation of a notification at a position on a wrist adherence portion corresponding with a row based, at least in part, on a notification status associated with the notification. The position on the wrist adherence portion corresponding with the row may indicate a notification status, a different notification status, and/or the like. For example, a representation of a notification displayed at a position corresponding with a row may indicate a notification status, and a representation of a different notification displayed at a position corresponding with a different row may indicate a different notification status. For example, a representation of a notification may be caused to be displayed within the same row as a representation of a different notification on the wrist adherence portion of the wrist worn apparatus. In such an example, the notification and the different notification may share a common notification status, may be associated with similar notification statuses, and/or the like. In this manner, the row may represent the notification status of the notifications associated with representations of notifications caused to be displayed at positions corresponding with the row.

In some circumstances, it may be desirable to arrange display of representations of notifications within a column based, at least in part, on notification status. For example, some users may be able to quickly distinguish between several notifications displayed in a column based, at least in part, on notification status. In at least one example embodiment, an apparatus causes display of a representation of a notification at a position on a wrist adherence portion corresponding with a column based, at least in part, on a notification status associated with the notification. The position on the wrist adherence portion corresponding with the column may indicate a notification status, a different notification status, and/or the like. For example, a representation of a notification displayed at a position corresponding with a column may indicate a notification status, and a representation of a different notification displayed at a position corresponding with a different column may indicate a different notification status. For example, a representation of a notification may be caused to be displayed within the same column as a representation of a different notification on the wrist adherence portion of the wrist worn apparatus. In such an example, the notification and the different notification may share a common notification status, may be associated with similar notification statuses, and/or the like. In this manner, the column may represent the notification status of the notifications associated with representations of notifications caused to be displayed at positions corresponding with the column.

In some circumstances, it may be desirable to arrange display of representations of notifications within a row based, at least in part, on notification type. For example, it may be desirable to group notifications that are associated with a common notification type into rows such that a user is easily able to perceive similar notifications at once, to determine a number of notifications of a particular type the user has available, and/or the like. In at least one example embodiment, an apparatus determines a position of a representation of a notification on a wrist adherence portion of a wrist worn apparatus based, at least in part, on a notification type. In at least one example embodiment, an apparatus causes display of a representation of a notification at a position on a wrist adherence portion corresponding with a row based, at least in part, on a notification type associated with the notification. The position on the wrist adherence portion corresponding with the row may indicate a notification type, a different notification type, and/or the like. For example, a representation of a notification displayed at a position corresponding with a row may indicate an application event, and a representation of a different notification displayed at a position corresponding with a different row may indicate a call event. For example, a representation of a notification may be caused to be displayed within the same row as a representation of a different notification on the wrist adherence portion of the wrist worn apparatus. In such an example, the notification and the different notification may share a common notification type, may be associated with similar notification types, and/or the like. In this manner, the row may represent notification types of the notifications associated with representations of notifications caused to be displayed at positions corresponding with the row.

In some circumstances, it may be desirable to arrange display of representations of notifications within a column based, at least in part, on notification type. For example, it may be desirable to group notifications that are associated with a common notification type into columns such that a user is easily able to perceive similar notifications at once, to determine a number of notifications of a particular type the user has available, and/or the like. In at least one example embodiment, an apparatus causes display of a representation of a notification at a position on a wrist adherence portion corresponding with a column based, at least in part, on a notification type associated with the notification. The position on the wrist adherence portion corresponding with the column may indicate a notification type, a different notification type, and/or the like. For example, a representation of a notification displayed at a position corresponding with a column may indicate an application event, and a representation of a different notification displayed at a position corresponding with a different column may indicate a call event. For example, a representation of a notification may be caused to be displayed within the same column as a representation of a different notification on the wrist adherence portion of the wrist worn apparatus. In such an example, the notification and the different notification may share a common notification type, may be associated with similar notification types, and/or the like. In this manner, the column may represent notification types of the notifications associated with representations of notifications caused to be displayed at positions corresponding with the column.

In many circumstances, a user may desire a position of a representation of a notification to change in a dynamic and intuitive manner. For example, the user may desire the position of the representation of the notification to change based, at least in part, on change in an associated notification status, receipt of one or more additional notifications, and/or the like. In at least one example embodiment, an apparatus determines that a notification status of a notification has changed to a different notification status. For example, the determination that the notification status of the notification has changed to the different notification status may based, at least in part, on the causation of display of a notification on a wrist adherence portion display of a wrist worn apparatus, display of the notification on a primary display of the wrist worn apparatus, receipt of information indicative of a notification selection input associated with the notification, and/or the like. In at least one example embodiment, an apparatus receives information indicative of a change of a notification status of a notification to a different notification status from a separate apparatus. In such an example embodiment, the determination that the notification status of the notification has changed to a different notification status may be based, at least in part, on the information indicative of the change of the notification status of the notification to the different notification status. In at least one example embodiment, an apparatus receives information indicative of a notification being read. The information indicative of the notification being read may be information indicating that a representation of the notification has been displayed by the apparatus, that a representation of the notification has been displayed by a separate apparatus, that the notification has been acknowledged by a user, and/or the like. In such an example embodiment, the determination that the notification status of the notification has changed to a different notification status may be based, at least in part, on the information indicative of the notification being read.

In order to provide for clear and quick identification of and distinguishment between a notification comprising a notification status and a notification comprising a different notification status, a user may desire to have representations of notifications grouped based, at least in part, on notification status. For example, the user may desire to have notifications comprising the notification status to be grouped together and displayed in one area, and notifications comprising the different notification status to be grouped together and displayed in a different area. For example, the user may desire to have representations of notifications associated with a notification status to be displayed in a more prominent region of a wrist adherence portion of a wrist worn apparatus, and to have representations of notifications associated with a different notification status to be displayed in a less prominent region of a wrist adherence portion of a wrist worn apparatus.

In at least one example embodiment, an apparatus determines a position of a representation of a notification on a wrist adherence portion of a wrist worn apparatus based, at least in part, on a notification status of the notification. In such an example embodiment, the notification status may change to a different notification status. In order to convey such a change in notification status to a user, the apparatus may move the representation of the notification to a different position.

In at least one example embodiment, an apparatus determines a different position of a representation of a notification on a wrist adherence portion of a wrist worn apparatus based, at least in part, on a different notification status. For example, the position of the representation of the notification on the wrist adherence portion of the wrist worn apparatus may be proximate to a first side of the primary display, and the different position of the representation of the notification on the wrist adherence portion of the wrist worn apparatus may be proximate to an opposite side of the primary display. In such an example, the position that is proximate to the first side of the primary display may be a position that is closer to an edge of the wrist adherence portion of the wrist worn apparatus that is proximate to the primary display than another edge of the wrist adherence portion, and the position that is proximate to the opposite side of the primary display may be a position that is closer to an edge of the wrist adherence portion of the wrist worn apparatus that is proximate to the primary display than another edge of the wrist adherence portion. In such an example, the position proximate to the first side of the primary display may be a position that is more prominent, more visible to the user, and/or the like. For example, the position proximate to the side of the primary display may be a position that is facing the user, that is on the top face of the wrist worn apparatus when the wrist worn apparatus is worn on the users wrist, and/or the like. In such an example, the position proximate to the opposite side of the primary display may be a position that is less prominent, less visible to the user, and/or the like. For example, the position proximate to the opposite side of the primary display may be a position that is facing away from the user, that is on the side face of the wrist worn apparatus when the wrist worn apparatus is worn on the users wrist, and/or the like.

In at least one example, a representation of a notification that has not yet been acknowledged by a user may be displayed at a more prominent position that may be proximate to the side of the primary display, and a representation of a different notification that has been acknowledged may be displayed at a less prominent position that may be proximate to the opposite side of the primary display. In another example, a position of a representation of a notification on a wrist adherence portion of a wrist worn apparatus may be proximate to a side of the primary display in circumstances where the notification status indicates a level of urgency that satisfies a threshold level of urgency. In such an example, a position of a representation of a different notification on the wrist adherence portion of the wrist worn apparatus may be proximate to an opposite side of the primary display in circumstances where the different notification status indicates a different level of urgency of the notification that fails to satisfy the threshold level of urgency. The threshold level of urgency may be a positive threshold, a negative threshold, and/or the like. For example, the representations of notifications that are associated with a level of urgency that is greater than the threshold level of urgency may be displayed at a more prominent position, at a position facing the user, and/or the like. The representations of notifications that are associated with a level of urgency that is less than the threshold level of urgency may be displayed at a less prominent position, at a position facing away from the user, and/or the like.

In some circumstances, as discussed previously, the wrist adherence portion of a wrist worn apparatus may comprise one or more bands. In such circumstances, a user may desire a notification to move from a first band to a second band, from a portion of a first band to a portion of a second band, and/or the like. In at least one example embodiment, a position of a representation of a notification on a wrist adherence portion of a wrist worn apparatus is a position on a first band portion. In such an example embodiment, an apparatus may determine a different position for display of the representation of the notification based, at least in part, on change of the notification status of the notification. For example, the different position of the representation of the notification on the wrist adherence portion of the wrist worn apparatus may be a position on a second band portion. For example, a position of a representation of a notification on a wrist adherence portion of a wrist worn apparatus may be a position on a first band portion in circumstances where the notification status indicates a level of urgency that satisfies a threshold level of urgency. In such an example, a different position of a representation of the notification on the wrist adherence portion of the wrist worn apparatus may be a position on a second band portion in circumstances where the notification status indicates a different level of urgency of the notification that fails to satisfy the threshold level of urgency. In such an example, an apparatus may cause display of the representation of the notification at the different position on the wrist adherence portion of the wrist worn apparatus. For example, the apparatus may cause display of the representation of the notification at the position on the second band portion based, at least in part, on a change in the level of urgency associated with the notification such that the level of urgency no longer satisfies the threshold level of urgency for display on the first band portion. As such, the apparatus may cause termination of display of the representation of the notification at the position, and cause display of the representation of the notification at the different position.

In the example of FIG. 3A, representation 326 is displayed at a position corresponding with a first row and a column, and representation 328 is displayed at a position corresponding with a second row and the column. The example of FIG. 3A depicts a single column, multiple row layout. Representations 326 and 328 may be displayed at a position corresponding with the first band portion based, at least in part, on notification type, notification status, notification time, and/or the like. For example, representations 326 and 328 may be associated with a level of urgency that satisfies a threshold level of urgency, which may cause display of the representations at a position on wrist adherence portion 304. Representations 322 and 324 may be displayed at a position corresponding with the second band portion based, at least in part, on a notification type, a notification status, a notification time, and/or the like. For example, representations 322 and 324 may be associated with a level of urgency that fails to satisfy the threshold level of urgency, which may cause display of the representations at a position on wrist adherence portion 302. Representation 326 may be displayed at a position closer to primary display 308 based, at least in part, on a notification type, a notification status, a notification time, and/or the like. For example, representation 326 may be associated with an event occurring before a different event associated with representation 328, occurring after a different event associated with representation 328, and/or the like. In another example, representation 326 may be associated with a level of urgency higher than a different level of urgency associated with representation 328, lower than a different level of urgency associated with representation 328, and/or the like. A color associated with each of representations 322, 324, 326, and 328 may indicate a notification type, a notification time, a notification status, and/or the like. For example, representation 326 may be shaded red to indicate that representation 326 is associated with an urgent system event. In another example, representation 322 may be shaded yellow to indicate that representation 322 is associated with a non-urgent weather application event.

In the example of FIG. 3B, representation 376 is displayed at a position corresponding with a first row and a third column on wrist adherence portion 354, and representation 378 is displayed at a position corresponding with a second row and a first column on wrist adherence portion 354. The example of FIG. 3B depicts a multiple column, multiple row layout. Although the example of FIG. 3B depicts three rows and three columns, the number of rows, columns, and/or the like, may vary. Representations 376 and 378 may be displayed at a position corresponding with the first band portion based, at least in part, on notification type, notification status, notification time, and/or the like. For example, representations 376 and 378 may be associated with a level of urgency that satisfies a threshold level of urgency, which may cause display of the representations at a position on wrist adherence portion 354. Representations 372 and 374 may be displayed at a position corresponding with the second band portion based, at least in part, on a notification type, a notification status, a notification time, and/or the like. For example, representations 372 and 374 may be associated with a level of urgency that fails to satisfy the threshold level of urgency, which may cause display of the representations at a position on wrist adherence portion 352. Representation 376 may be displayed at a position closer to primary display 358 that the different representation corresponding with the second row and the third column based, at least in part, on a notification type, a notification status, a notification time, and/or the like. For example, representation 376 may be associated with an event occurring before a different event associated with the different representation, occurring after a different event associated with the different representation, and/or the like. In another example, representation 376 may be associated with a level of urgency higher than a different level of urgency associated with representation 378, lower than a different level of urgency associated with representation 378, and/or the like. In yet another example, representations 376 and 378 may be displayed at a position corresponding with wrist adherence portion 354 based, at least in part, on an unread notification status, and representations 372 and 374 may be displayed at a position corresponding with wrist adherence portion 352 based, at least in part, on an read notification status. A color associated with each of representations 372, 374, 376, and 378 may indicate a notification type, a notification time, a notification status, and/or the like. For example, representation 376 may be shaded red to indicate that representation 376 is associated with an urgent system event. In another example, representation 372 may be shaded yellow to indicate that representation 372 is associated with a non-urgent weather application event.

In the example of FIG. 3B, representation 374 and 376 are displayed at positioned corresponding with the third column of wrist adherence portions 352 and 354, respectively. Causing display of a representation of a notification at a position corresponding with a specific column may indicate a notification type of the notification being displayed in the column. For example, the first column may indicate that the notification is associated with a system event, the second column may indicate that the notification is associated with a call event, and the third column may indicate that the notification is associated with a text event. In such an example, representation 372 may be associated with a call event, representation 378 may be associated with a system event, and representations 374 and 376 may be associated with text event. The display of representation 376 at a position on the second band portion and the third column may indicate that representation 376 is associated with an acknowledged notification pertaining to a text event, the display of representation 378 at a position on the first band portion and the first column may indicate that representation 378 is associated with an unacknowledged notification pertaining to a system event, and/or the like.

Although the examples of FIGS. 3A-3B depict the representations of the notifications as solid horizontal bars displayed on a wrist adherence portion display, the configuration of the displays, the orientation of the representations of the notifications, the design of the representations of the notifications, the number of rows, the number of columns, and/or the like, may vary. For example, the representations of the notifications may be dashed vertical bars, dotted line, circles, and/or the like.

FIGS. 4A-4B are diagrams illustrating information for display on a primary display of a wrist worn apparatus according to at least one example embodiment. The examples of FIGS. 4A-4B are merely examples and do not limit the scope of the claims. For example, primary display configuration may vary, notifications may vary, representations of notifications may vary, display of representations of notifications may vary, display of notifications may vary, information displayed by a primary display may vary, and/or the like.

In some circumstances, a user may desire to view a representation of a notification that is different from a representation of the notification that is displayed via a wrist adherence portion display. For example, although initial display of the representation of the notification via the wrist adherence portion display may be desirable for the reasons discussed previously, a user may desire to view additional details associated with the notification by way of a different display. For example, the wrist adherence portion display may not be optimized for display of text, may not be tailored for display of visual information, and/or the like. In at least one example embodiment, an apparatus receives information indicative of a notification selection input associated with a notification. For example, the notification selection input may be a tap input at a position on the wrist adherence portion of the wrist worn apparatus that corresponds with the position of the representation of the notification. In at least one example embodiment, an apparatus causes display of a different representation of the notification on the primary display of the wrist worn apparatus based, at least in part, on the notification selection input.

For example, a user may receive a notification associated with an urgent call event. In such an example, the user may desire to have a representation of the notification displayed via a wrist adherence portion of the user's wrist worn apparatus such that the user is readily able to identify that the notification is urgent and that the notification pertains to a call event. The user may tap at a position on the wrist adherence portion that corresponds with the position of display of the representation of the notification in order to have a different representation of the notification displayed on the primary display of the user's wrist worn apparatus. The different representation of the notification may comprise text information, visual information, identification information, contact information, application information, time information, etc., pertaining to the notification, the event, and/or the like.

FIG. 4A is a diagram illustrating information for display on a primary display of a wrist worn apparatus according to at least one example embodiment. The example of FIG. 4A depicts primary display 402 displaying home screen 404. In the example of FIG. 4A, home screen 404 is configured to display clock and calendar information, which may be particularly desirable for a user of a wrist worn apparatus to view on a regular basis. Although the example of FIG. 4A depicts a home screen configured to display clock and calendar information, home screen content may vary, home screen configuration may vary, and/or the like.

FIG. 4B is a diagram illustrating a representation of a notification for display on a primary display of a wrist worn apparatus according to at least one example embodiment. The example of FIG. 4B depicts primary display 412 displaying representation 414. Representation 414 may be a different representation of a notification displayed on the wrist adherence portion of the wrist worn apparatuses depicted in FIGS. 3A-3B. For example, representation 414 may be caused to be displayed on primary display 412 based, at least in part, on receipt of information indicative of a notification selection input associated with representation 372 of FIG. 3B. As such, the second column of representations of notifications depicted in FIG. 4B may be associated with call events, and receipt of a notification selection input at a position corresponding with one of the representations of the notifications may cause display of a different representation of the call event notification. Although the example of FIG. 4B depicts a representation of a notification configured to display notification type and contact information associated with the call event, content of the notification may vary, configuration of the representation of the notification may vary, and/or the like.

Figure 5:
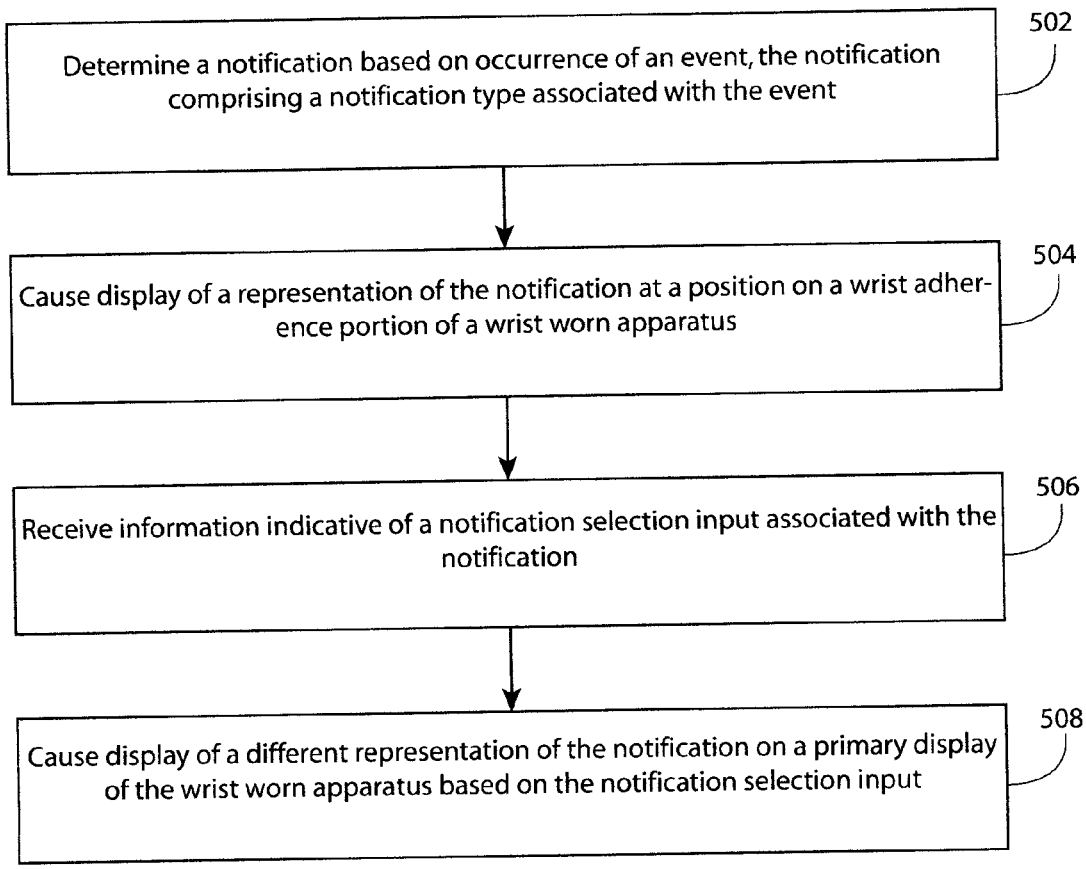
FIG. 5 is a flow diagram illustrating activities associated with causation of display of a representation of a notification on a primary display of a wrist worn apparatus according to at least one example embodiment.

FIG. 5 is a flow diagram illustrating activities associated with causation of display of a representation of a notification on a primary display of a wrist worn apparatus according to at least one example embodiment. In at least one example embodiment, there is a set of operations that corresponds with the activities of FIG. 5. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 5.

At block 502, the apparatus determines a notification based, at least in part, on occurrence of an event, the notification comprising a notification type associated with the event. The determination, the notification, the occurrence of the event, and the notification type may be similar as described regarding FIGS. 2A-2D, FIGS. 3A-3B, and FIGS. 4A-4B.

At block 504, the apparatus causes display of a representation of the notification at a position on a wrist adherence portion of a wrist worn apparatus, the wrist adherence portion being distinct from a primary display, and the representation of the notification being indicative of the notification type. The causation of display, the representation of the notification, the wrist worn apparatus, the wrist adherence portion of the wrist worn apparatus, the position on the wrist adherence portion on the wrist worn apparatus, and the primary display may be similar as described regarding FIGS. 2A-2D, FIGS. 3A-3B, and FIGS. 4A-4B.

At block 506, the apparatus receives information indicative of a notification selection input associated with the notification. The receipt of information and the notification selection input associated with the notification may be similar as described regarding FIGS. 2A-2D, FIGS. 3A-3B, and FIGS. 4A-4B.

At block 508, the apparatus causes display of a different representation of the notification on the primary display of the wrist worn apparatus based, at least in part, on the notification selection input. The causation of display and the different representation of the notification may be similar as described regarding FIGS. 2A-2D, FIGS. 3A-3B, and FIGS. 4A-4B.

Figure 6:
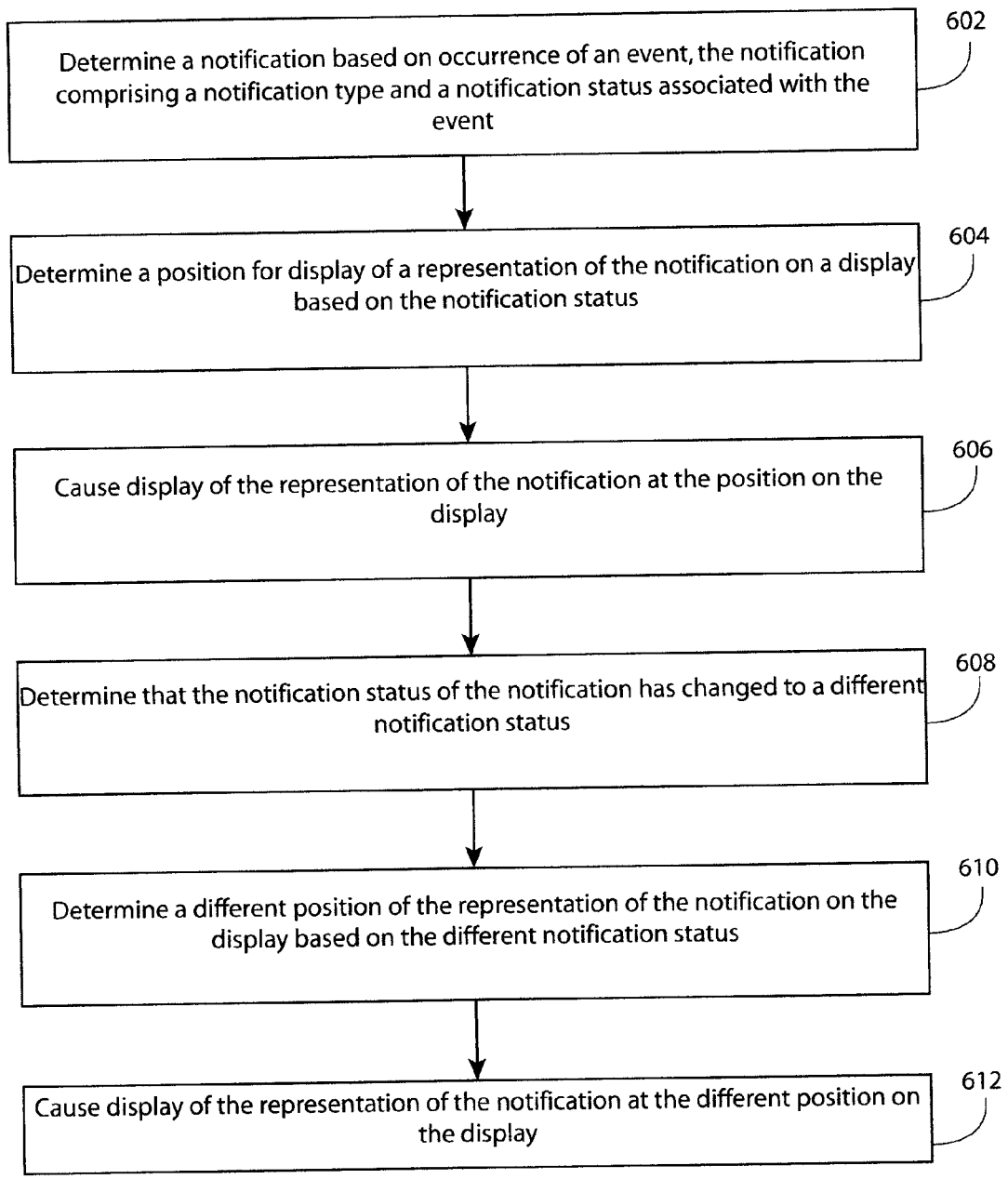
FIG. 6 is a flow diagram illustrating activities associated with causation of display of a representation of a notification at a different position according to at least one example embodiment.

FIG. 6 is a flow diagram illustrating activities associated with causation of display of a representation of a notification at a different position according to at least one example embodiment. In at least one example embodiment, there is a set of operations that corresponds with the activities of FIG. 6. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 6.

As discussed previously, in some circumstances, it may be desirable to cause display of a representation of a notification at a position that is based, at least in part, on a notification status associated with the notification. In such circumstances, it may be desirable to cause display of the representation of the notification at a different position based, at least in part, on change of the notification status associated with the notification.

At block 602, the apparatus determines a notification based, at least in part, on occurrence of an event, the notification comprising a notification type and a notification status associated with the event. The determination, the notification, the occurrence of the event, the notification type, and the notification status may be similar as described regarding FIGS. 2A-2D, FIGS. 3A-3B, and FIGS. 4A-4B.

At block 604, the apparatus determines a position for display of a representation of the notification on a display based, at least in part, on the notification status. The determination, the position, the representation of the notification, and the display may be similar as described regarding FIGS. 2A-2D, FIGS. 3A-3B, and FIGS. 4A-4B.

At block 606, the apparatus causes display of the representation of the notification at the position on the display. The causation of display of the representation of the notification at the position on the display may be similar as described regarding FIGS. 2A-2D, FIGS. 3A-3B, and FIGS. 4A-4B.

At block 608, the apparatus determines that the notification status of the notification has changed to a different notification status. The determination, the different notification status, and the change to the different notification status may be similar as described regarding FIGS. 2A-2D, FIGS. 3A-3B, and FIGS. 4A-4B.

At block 610, the apparatus determines a different position for display of the representation of the notification on the display based, at least in part, on the different notification status. The determination and the different position of the representation of the notification on the display may be similar as described regarding FIGS. 2A-2D, FIGS. 3A-3B, and FIGS. 4A-4B.

At block 612, the apparatus causes display of the representation of the notification at the different position on the display. The causation of display and the display of the representation of the notification at the different position on the display may be similar as described regarding FIGS. 2A-2D, FIGS. 3A-3B, and FIGS. 4A-4B.

Figure 7:
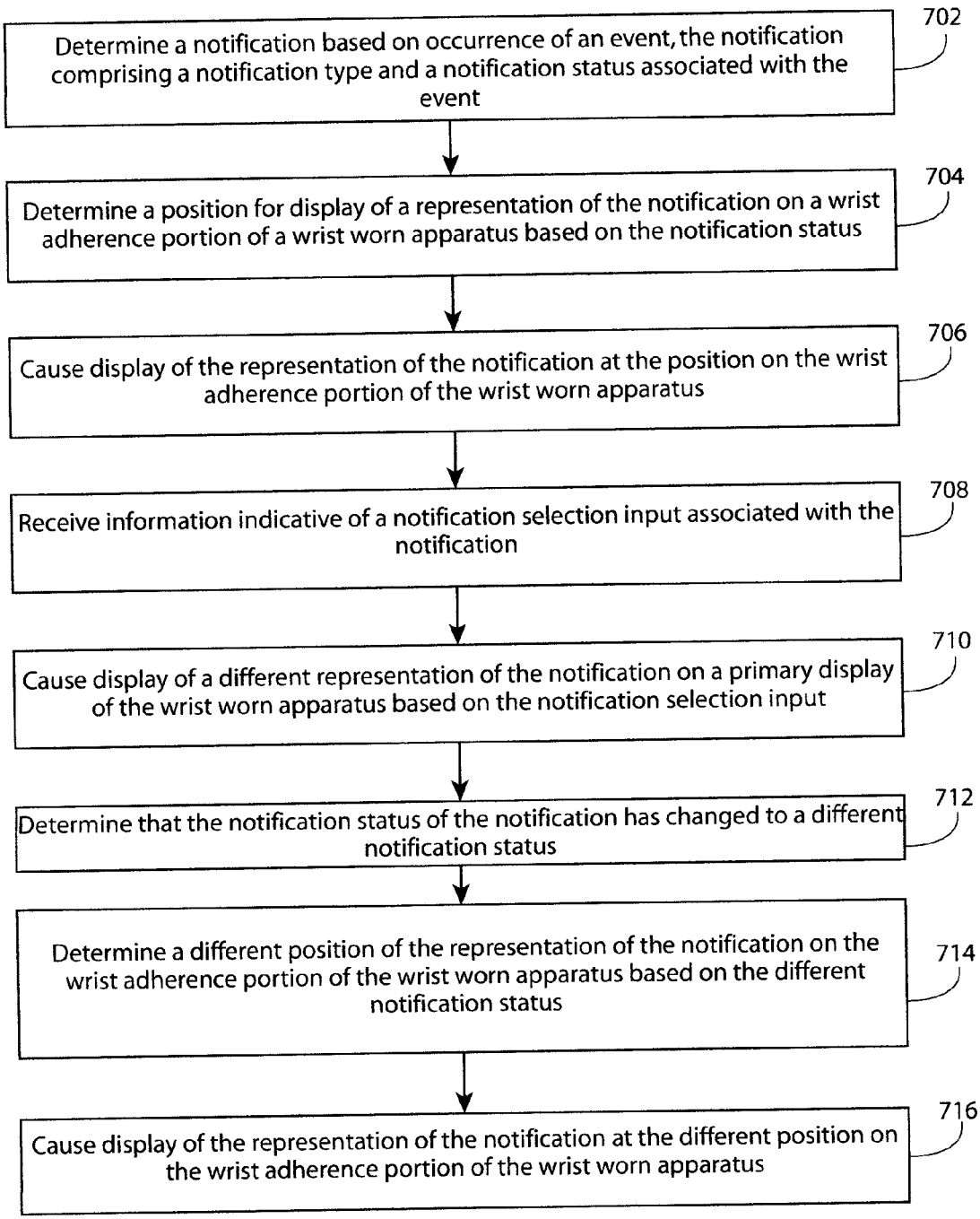
FIG. 7 is a flow diagram illustrating activities associated with causation of display of a representation of a notification at a different position on a wrist adherence portion of a wrist worn apparatus according to at least one example embodiment.

FIG. 7 is a flow diagram illustrating activities associated with causation of display of a representation of a notification at a different position on a wrist adherence portion of a wrist worn apparatus according to at least one example embodiment. In at least one example embodiment, there is a set of operations that corresponds with the activities of FIG. 7. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 7.

As discussed previously, in some circumstances, it may be desirable to cause display of a representation of a notification at a position on a wrist adherence portion of a wrist worn apparatus that is based, at least in part, on a notification status associated with the notification. In such circumstances, it may be desirable to cause display of the representation of the notification at a different position on the wrist adherence portion of the wrist worn apparatus based, at least in part, on change of the notification status associated with the notification.

At block 702, the apparatus determines a notification based, at least in part, on occurrence of an event, the notification comprising a notification type and a notification status associated with the event. The determination, the notification, the occurrence of the event, the notification type, and the notification status may be similar as described regarding FIGS. 2A-2D, FIGS. 3A-3B, and FIGS. 4A-4B.

At block 704, the apparatus determines a position for display of a representation of the notification on a wrist adherence portion of a wrist worn apparatus based, at least in part, on the notification status. The determination, the position, the representation of the notification, the wrist worn apparatus, and the wrist adherence portion of the wrist worn apparatus may be similar as described regarding FIGS. 2A-2D, FIGS. 3A-3B, and FIGS. 4A-4B.

At block 706, the apparatus causes display of the representation of the notification at the position on the wrist adherence portion of the wrist worn apparatus. The causation of display of the representation of the notification at the position on the wrist adherence portion of the wrist worn apparatus may be similar as described regarding FIGS. 2A-2D, FIGS. 3A-3B, and FIGS. 4A-4B.

At block 708, the apparatus receives information indicative of a notification selection input associated with the notification. The receipt of information and the notification selection input associated with the notification may be similar as described regarding FIGS. 2A-2D, FIGS. 3A-3B, and FIGS. 4A-4B.

At block 710, the apparatus causes display of a different representation of the notification on a primary display of the wrist worn apparatus based, at least in part, on the notification selection input. The causation of display, the different representation of the notification, the primary display, and the display of the different representation of the notification on the primary display may be similar as described regarding FIGS. 2A-2D, FIGS. 3A-3B, and FIGS. 4A-4B.

At block 712, the apparatus determines that the notification status of the notification has changed to a different notification status. The determination, the different notification status, and the change to the different notification status may be similar as described regarding FIGS. 2A-2D, FIGS. 3A-3B, and FIGS. 4A-4B.

At block 714, the apparatus determines a different position for display of the representation of the notification on the wrist adherence portion of the wrist worn apparatus based, at least in part, on the different notification status. The determination and the different position for display of the representation of the notification on the wrist adherence portion of the wrist worn apparatus may be similar as described regarding FIGS. 2A-2D, FIGS. 3A-3B, and FIGS. 4A-4B.

At block 716, the apparatus causes display of the representation of the notification at the different position on the wrist adherence portion of the wrist worn apparatus. The causation of display and the display of the representation of the notification at the different position on the wrist adherence portion of the wrist worn apparatus may be similar as described regarding FIGS. 2A-2D, FIGS. 3A-3B, and FIGS. 4A-4B.

Figure 8:
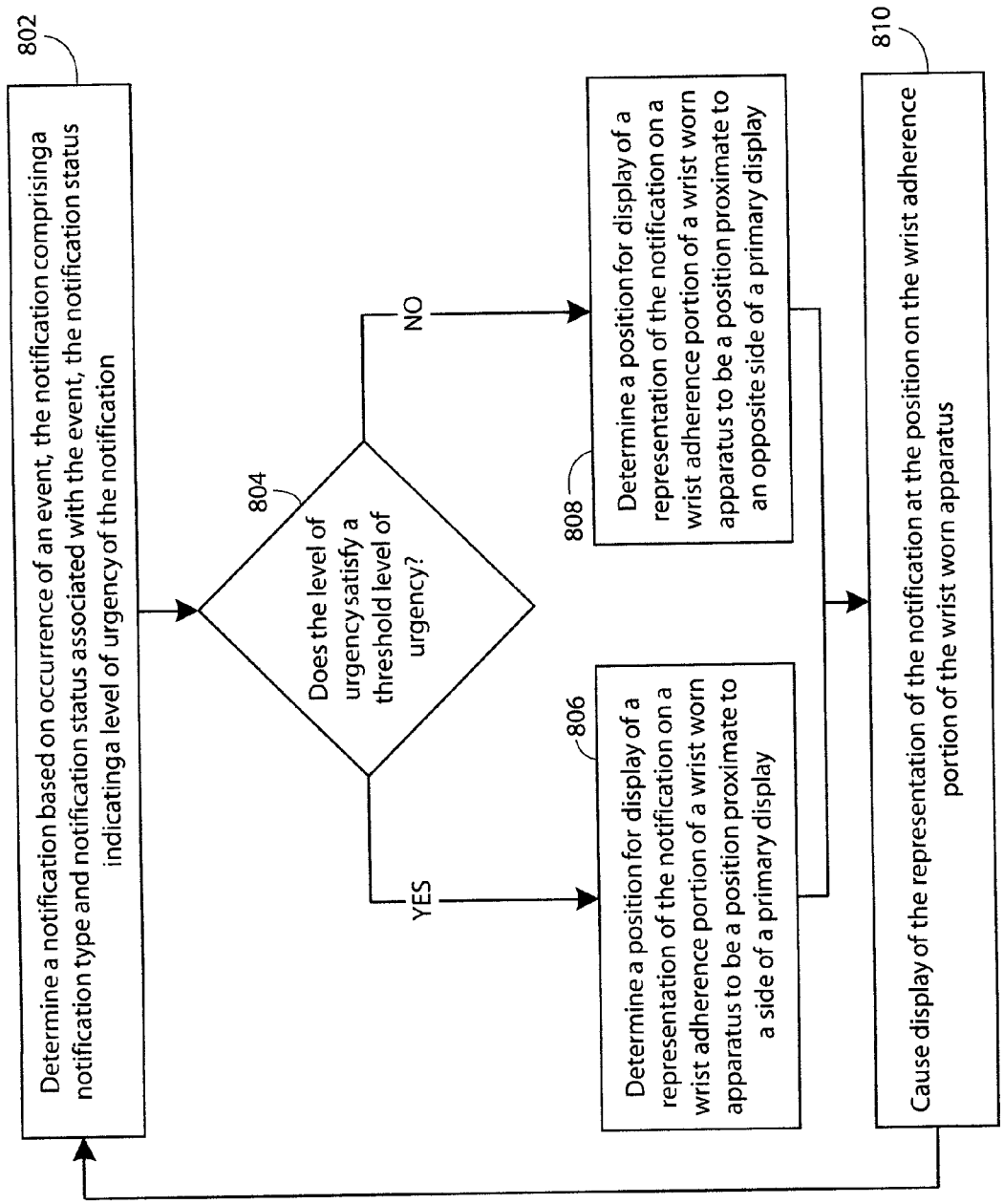
FIG. 8 is a flow diagram illustrating activities associated with determination of a position for display of a representation of a notification based on a level of urgency according to at least one example embodiment.

FIG. 8 is a flow diagram illustrating activities associated with determination of a position for display of a representation of a notification based on a level of urgency according to at least one example embodiment. In at least one example embodiment, there is a set of operations that corresponds with the activities of FIG. 8. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 8.

As discussed previously, in some circumstances, it may be desirable to cause display of a representation of a notification at a position on a wrist adherence portion of a wrist worn apparatus that is based, at least in part, on a notification status associated with the notification. For example, it may be desirable to cause display of a representation of a notification at a position on a wrist adherence portion of a wrist worn apparatus that is on a side of a primary display, an opposite side of the primary display, and/or the like, that is based, at least in part, on a level of urgency associated with the notification. In such circumstances, it may be desirable to cause display of the representation of the notification on a different side of the primary display based, at least in part, on change of the level of urgency associated with the notification.

At block 802, the apparatus determines a notification based, at least in part, on occurrence of an event, the notification comprising a notification type and a notification status associated with the event, and the notification status indicating a level of urgency of the notification. The determination, the notification, the occurrence of the event, the notification type, the notification status, and the level of urgency of the notification may be similar as described regarding FIGS. 2A-2D, FIGS. 3A-3B, and FIGS. 4A-4B.

At block 804, the apparatus determines whether the level of urgency satisfies a threshold level of urgency. If the apparatus determines that the level of urgency satisfies the threshold level of urgency, flow proceeds to block 806. If the apparatus determines that the level of urgency fails to satisfy the threshold level of urgency, flow proceeds to block 808. The determination and the threshold level of urgency may be similar as described regarding FIGS. 2A-2D, FIGS. 3A-3B, and FIGS. 4A-4B.

At block 806, the apparatus determines a position for display of a representation of the notification on a wrist adherence portion of a wrist worn apparatus to be a position proximate to a side of a primary display. The determination, the representation of the notification, the wrist worn apparatus, the wrist adherence portion of the wrist worn apparatus, the display of the representation of the notification on the wrist adherence portion of the wrist worn apparatus, the primary display, the side of the primary display, and the position proximate to the side of the primary display may be similar as described regarding FIGS. 2A-2D, FIGS. 3A-3B, and FIGS. 4A-4B.

At block 808, the apparatus determines a position for display of a representation of the notification on the wrist adherence portion of the wrist worn apparatus to be a position proximate to an opposite side of the primary display. The determination, the representation of the notification, the wrist worn apparatus, the wrist adherence portion of the wrist worn apparatus, the display of the representation of the notification on the wrist adherence portion of the wrist worn apparatus, the primary display, the opposite side of the primary display, and the position proximate to the opposite side of the primary display may be similar as described regarding FIGS. 2A-2D, FIGS. 3A-3B, and FIGS. 4A-4B.

At block 810, the apparatus causes display of the representation of the notification at the position on the wrist adherence portion of the wrist worn apparatus. The causation of display and the display of the representation of the notification at the position on the wrist adherence portion of the wrist worn apparatus may be similar as described regarding FIGS. 2A-2D, FIGS. 3A-3B, and FIGS. 4A-4B.

Embodiments of the invention may be implemented in software, hardware, application logic or a combination of software, hardware, and application logic. The software, application logic and/or hardware may reside on the apparatus, a separate device, or a plurality of separate devices. If desired, part of the software, application logic and/or hardware may reside on the apparatus, part of the software, application logic and/or hardware may reside on a separate device, and part of the software, application logic and/or hardware may reside on a plurality of separate devices. In an example embodiment, the application logic, software or an instruction set is maintained on any one of various conventional computer-readable media.

If desired, the different functions discussed herein may be performed in a different order and/or concurrently with each other. For example, block 710 of FIG. 7 may be performed after block 712 of FIG. 7. Furthermore, if desired, one or more of the above-described functions may be optional or may be combined. For example, block 608 of FIG. 6 may be optional and/or combined with block 610 of FIG. 6.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes example embodiments of the invention, these descriptions should not be viewed in a limiting sense. Rather, there are variations and modifications which may be made without departing from the scope of the present invention as defined in the appended claims.

What is claimed is:

1. An apparatus, comprising:
    at least one processor;
    at least one memory including computer program code, the memory and the computer program code configured to, working with the processor, cause the apparatus to perform at least the following:
        determine a notification based on occurrence of an event, the notification comprising a notification type associated with the event;
        cause display of a representation of the notification at a position on a wrist adherence portion of a wrist worn apparatus, the wrist adherence portion being distinct from a primary display, and the representation of the notification being indicative of the notification type, wherein the position of the notification on the wrist adherence portion is determined to be closer or further from the primary display based on a notification status;
        receive information indicative of a notification selection input associated with the notification; and
        cause display of a different representation of the notification on the primary display of the wrist worn apparatus in response to the notification selection input, wherein the different representation comprises additional details relative to detail of the representation of the notification on the wrist adherence portion.

2. The apparatus of claim 1, wherein the position on the wrist adherence portion on which the notification is displayed is determined based on a notification status associated with the notification.

3. The apparatus of claim 1, wherein the memory includes computer program code configured to, working with the processor, cause the apparatus to perform identification of a notification attribute associated with the notification.

4. The apparatus of claim 1, wherein a color of the representation of the notification is indicative of at least one of a level of urgency, a time, an application, an importance, a count of associated notifications, a notification status, or the notification type.

5. The apparatus of claim 1, wherein the notification comprises a notification status, and wherein the memory includes computer program code configured to, working with the processor, cause the apparatus to perform determination of the position of the representation of the notification on the wrist adherence portion of the wrist worn apparatus relative to other notifications represented on the wrist adherence portion, based on the notification status.

6. The apparatus of claim 5, wherein the memory includes computer program code configured to, working with the processor, cause the apparatus to perform:
    determine that the notification status of the notification has changed to a different notification status;
    determine a different position of the representation of the notification on the wrist adherence portion of the wrist worn apparatus based on the different notification status; and
    cause display of the representation of the notification at the different position on the wrist adherence portion of the wrist worn apparatus.

7. The apparatus of claim 1, wherein the position is determined to be on one side of the primary display or the other side of the primary display based on a notification status.

8. The apparatus of claim 5, wherein the notification status indicates a level of urgency of the notification, and the determination of the position of the representation of the notification on the wrist adherence portion of the wrist worn apparatus is further based on the level of urgency.

9. A method comprising:
    determining a notification based on occurrence of an event, the notification comprising a notification type associated with the event;
    causing display of a representation of the notification at a position on a wrist adherence portion of a wrist worn apparatus, the wrist adherence portion being distinct from a primary display, and the representation of the notification being indicative of the notification type, wherein the position of the notification on the wrist adherence portion is determined to be closer or further from the primary display based on a notification status;
    receiving information indicative of a notification selection input associated with the notification; and
    causing display of a different representation of the notification on the primary display of the wrist worn apparatus in response to the notification selection input, wherein the different representation comprises additional details relative to detail of the representation of the notification on the wrist adherence portion.

10. The method of claim 9, further comprising identifying a notification attribute associated with the notification.

11. The method of claim 9, wherein a color of the representation of the notification is indicative of at least one of a level of urgency, a time, an application, an importance, a count of associated notifications, a notification status, or the notification type.

12. The method of claim 9, wherein the notification comprises a notification status, and further comprising determining the position of the representation of the notification on the wrist adherence portion of the wrist worn apparatus relative to other notifications represented on the wrist adherence portion, based on the notification status.

13. The method of claim 12, further comprising:
    determining the notification status of the notification has changed to a different notification status;
    determining a different position of the representation of the notification on the wrist adherence portion of the wrist worn apparatus based on the different notification status; and
    causing display of the representation of the notification at the different position on the wrist adherence portion of the wrist worn apparatus.

14. The method of claim 9, wherein the position is determined to be on one side of the primary display or the other side of the primary display based on a notification status.

15. At least one non-transitory computer-readable medium encoded with instructions that, when executed by a processor, perform:
    determining a notification based on occurrence of an event, the notification comprising a notification type associated with the event;
    causing display of a representation of the notification at a position on a wrist adherence portion of a wrist worn apparatus, the wrist adherence portion being distinct from a primary display, and the representation of the notification being indicative of the notification type, wherein the position of the notification on the wrist adherence portion is determined to be closer or further from the primary display based on a notification status;
    receiving information indicative of a notification selection input associated with the notification; and causing display of a different representation of the notification on the primary display of the wrist worn apparatus in response to the notification selection input, wherein the different representation comprises additional details relative to detail of the representation of the notification on the wrist adherence portion.

16. The non-transitory computer-readable medium of claim 15, wherein a color of the representation of the notification is indicative of at least one notification attribute associated with the notification.

17. The non-transitory computer-readable medium of claim 15, wherein the notification comprises a notification status, and wherein the non-transitory computer-readable medium is further encoded with instructions that, when executed by a processor, perform determining the position of the representation of the notification on the wrist adherence portion of the wrist worn apparatus based, at least in part, on the notification status.

18. The non-transitory computer-readable medium of claim 17, wherein the medium is further encoded with instructions that, when executed by the processor, perform:
  determining the notification status of the notification has changed to a different notification status;
  determining a different position of the representation of the notification on the wrist adherence portion of the wrist worn apparatus based, at least in part, on the different notification status; and
  causing display of the representation of the notification at the different position on the wrist adherence portion of the wrist worn apparatus.

19. The apparatus of claim 1, wherein the position of the notification on the wrist adherence portion is within at least one of a row or a column, wherein the at least one of the row or the column is determined based on a notification attribute associated with the notification.

* * * * *